US011421204B2

(12) United States Patent
Yoshida et al.

(10) Patent No.: US 11,421,204 B2
(45) Date of Patent: Aug. 23, 2022

(54) METHOD OF REMOVING PLURIPOTENT CELLS FROM CULTURE

(71) Applicants: REPROCELL INCORPORATED, Yokohama (JP); SBI PHARMACEUTICALS CO., LTD., Tokyo (JP)

(72) Inventors: Shunsuke Yoshida, Yokohama (JP); Mitsuru Inamura, Yokohama (JP); Tohru Tanaka, Tokyo (JP); Hiroyuki Ishikawa, Tokyo (JP); Hidenori Ito, Tokyo (JP)

(73) Assignees: REPROCELL INCORPORATED, Yokohama (JP); SBI PHARMACEUTICALS CO., LTD., Tokyo (JP)

( * ) Notice: Subject to any disclaimer, the term of this patent is extended or adjusted under 35 U.S.C. 154(b) by 645 days.

(21) Appl. No.: 15/565,422

(22) PCT Filed: Apr. 6, 2016

(86) PCT No.: PCT/JP2016/061189
§ 371 (c)(1),
(2) Date: Oct. 9, 2017

(87) PCT Pub. No.: WO2016/163374
PCT Pub. Date: Oct. 13, 2016

(65) Prior Publication Data
US 2018/0127726 A1  May 10, 2018

(30) Foreign Application Priority Data
Apr. 7, 2015 (JP) .............................. JP2015-078170

(51) Int. Cl.
C12N 5/00 (2006.01)
C12N 5/16 (2006.01)
C12N 1/02 (2006.01)
C12N 5/10 (2006.01)
C12N 1/00 (2006.01)
C07C 233/56 (2006.01)

(52) U.S. Cl.
CPC .............. C12N 5/16 (2013.01); C07C 233/56 (2013.01); C12N 1/00 (2013.01); C12N 1/02 (2013.01); C12N 5/0081 (2013.01); C12N 5/10 (2013.01); C12N 2500/32 (2013.01); C12N 2529/10 (2013.01)

(58) Field of Classification Search
CPC ... C12N 5/16; C12N 1/00; C12N 1/02; C12N 5/10; C12N 2500/32; C12N 2529/10; C07C 233/56
See application file for complete search history.

(56) References Cited

U.S. PATENT DOCUMENTS

2014/0128799 A1   5/2014  Tanaka et al.
2015/0376568 A1  12/2015  Tateno et al.
2016/0040123 A1   2/2016  Kanemura et al.

FOREIGN PATENT DOCUMENTS

| JP | 2014-023457 A | 2/2014 |
| KR | 10-1449599 | 10/2014 |
| WO | WO2013005379 | 1/2013 |
| WO | WO2014126146 | 8/2014 |
| WO | WO2014157257 | 10/2014 |

OTHER PUBLICATIONS

"CSCs and pluripotent/multipotentstem cells." Lab Invest 97, 1124-1125 (2017).*
Ritter et al., An Bras Dermatol. 2010;85(5):639-45.*
Schriebl et al., Tissue Engineering, Part A, 18(9-10), 899-909, 2012.*
AlSalhi et al., Laser Physics, 2011, vol. 21, No. 4, pp. 733-739.*
Yoo et al., International Review of Cell and Molecular Biology, vol. 295, 2012, Chapter four—New Insights into the Mechanisms for Photodynamic Therapy-Induced Cancer Cell Death pp. 139-174.*
Yano et al: "Photodynamic therapy as salvage treatment for local failures after definitive chemoradiotherapy for esophageal cancer", Gastrointestinal Endosc, Elsevier, NL, vol. 62, No. 1, Jul. 1, 2005 (Jul. 1, 2005), pp. 31-36, XP005284947, ISSN: 0016-5107, DOI: 10.1016/S0016-5107(05)00545-6 * p. 32, col. 2, paragraph 2.
Chuan-Hang Yu et al: "Photodynamic Therapy with 5-Aminolevulinic acid (ALA) Impairs Tumor Initiating and Chemo-Resistance Property in Head and Neck Cancer-Derived Cancer Stem Cells", PLOS ONE, vol. 9, No. 1, Jan. 24, 2014 (Jan. 24, 2014), p. e87129, XP055395499, DOI: 10.1371/journal.pone.0087129 * figures 1-3 *.
Mohammadpour Hemn et al: "Antitumor effect of conditioned media derived from murine MSCs and 5-aminolevulinic acid (5-ALA) mediated photodynamic therapy in breast cancer in vitro", Photodiagnosis and Photodynamic Therapy, vol. 12, No. 2, Feb. 24, 2015 (Feb. 24, 2015), pp. 238-243, XP029237254, ISSN: 1572-1000, DOI: 10.1016/J.PDPDT.2015.02.004 * p. 240, col. 1, paragraph 2 *.

(Continued)

Primary Examiner — Michael C Wilson
(74) Attorney, Agent, or Firm — Hawaii Patent Services; Nathaniel K. Fedde

(57) ABSTRACT

A stem cell removing method that certainly-removes an undifferentiated stem cell is provided. For this object, a cell group including a stem cell and a somatic cell performed differentiation induction is cultivated in culture medium composition including photosensitizer. Light of a specific wavelength is irradiated with the cell group, and the stem cell is removed, selectively. The stem cell is a pluripotent stem cell or a somatic stem cell. The pluripotent stem cell includes either an ES cell (Embryonic Stem Cell) or an iPS cell (induced Pluripotent Stem Cell). Also, somatic stem cell includes any one of a germ stem cell, a productive cell, a pluripotent stem cell and a stem cell having unipotency.

8 Claims, 18 Drawing Sheets

(56) References Cited

OTHER PUBLICATIONS

Zhang Baoqin et al., Toxicity to the normal hemocytes by ALA-PDT for the ex vivo purging of hematopoietic stem cell grafts, Academic Journal of Xi'an jiaotong University, 2008, vol. 20, No. 4, p. 250-255, abstract, Material and methods 4, Fig. 1, 2, Result 1-3, p. 254, right column.
Susanto, Jimmy et al., Porphyrin ZHomeostasis Maintained by ABCG2 Regulates Self-Renewal of Embryonic Stem Cells, PLos ONE, 2008, vol. 3, No. 12, e4023, p. 5, left column, Fig. 5D.
Venosa et al. "Photodynamic therapy: Regulation of porphyrin synthesis and hydrolysis from ALA esters" Journal of Photochemistry and Photobiology B Biology 83 (2006) 129-136.
Baglo et al. "Homology Modeling of Human c-Butyric Acid Transporters and the Binding of Pro-Drugs 5-Aminolevulinic Acid and Methyl Aminolevulinic Acid Used in Photodynamic Therapy"; PLOS ONE 8(6) Jun. 2013, vol. 8, Issue 6, e65200.
Rahman et al., "Stem Cell and Cancer Stem Cell: A Tale of Two Cells." 2016. Progress in stem cells: 3(2)-97-108).
"Pluripotent" entry in Henderson's Dictionary of Biology, 15th Edition. 2010. Pearson Education Limited, Edited by Eleanor Lawrence.
Zhang et al. "Photodynamic therapy regulates fate of cancer stem cells through reactive oxygen species" World J Stem Cells Jul. 26, 2020; 12(7): 527-705.

\* cited by examiner

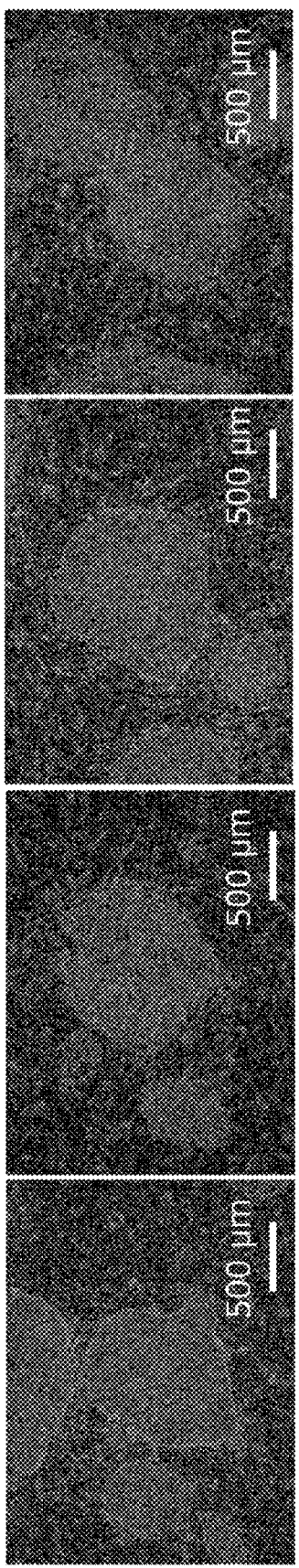
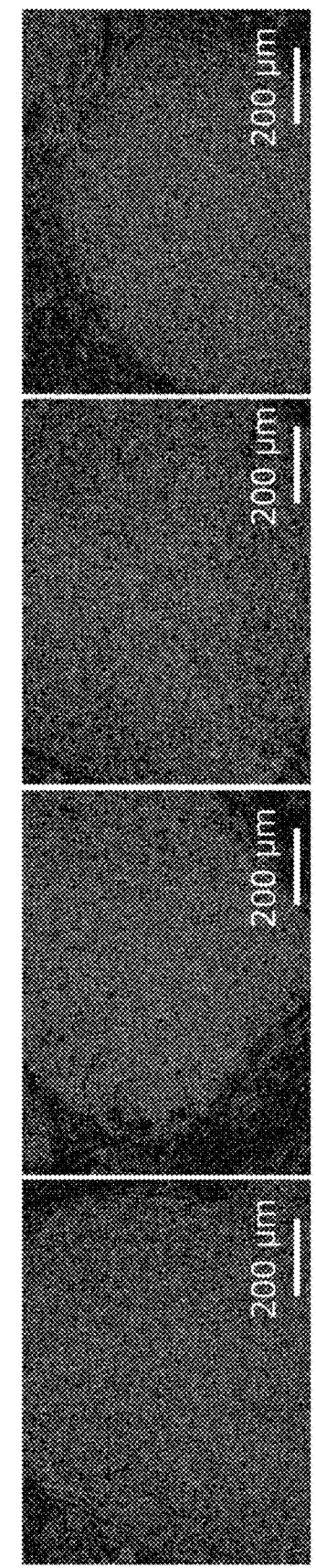
FIG.7 ALA ADDITION + PHOTOIRRADIATION (FOR 10 MINUTES) 24 HOURS

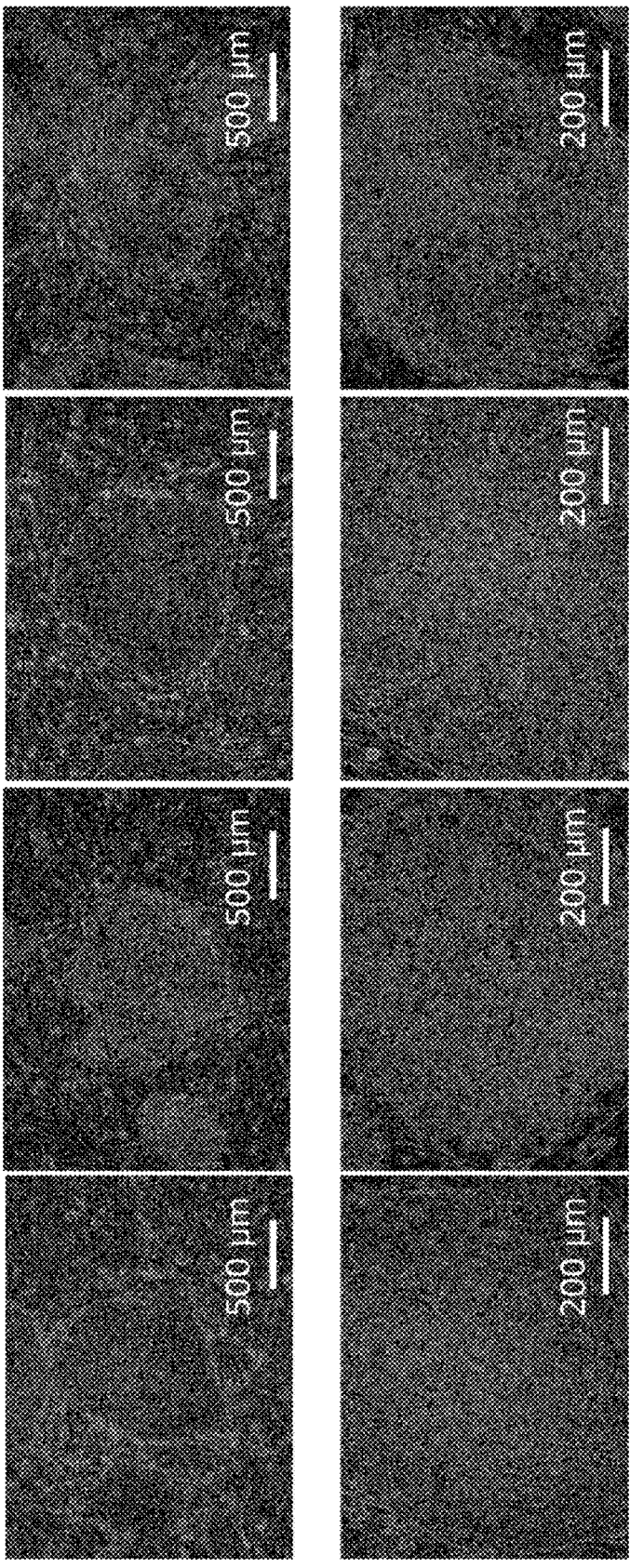

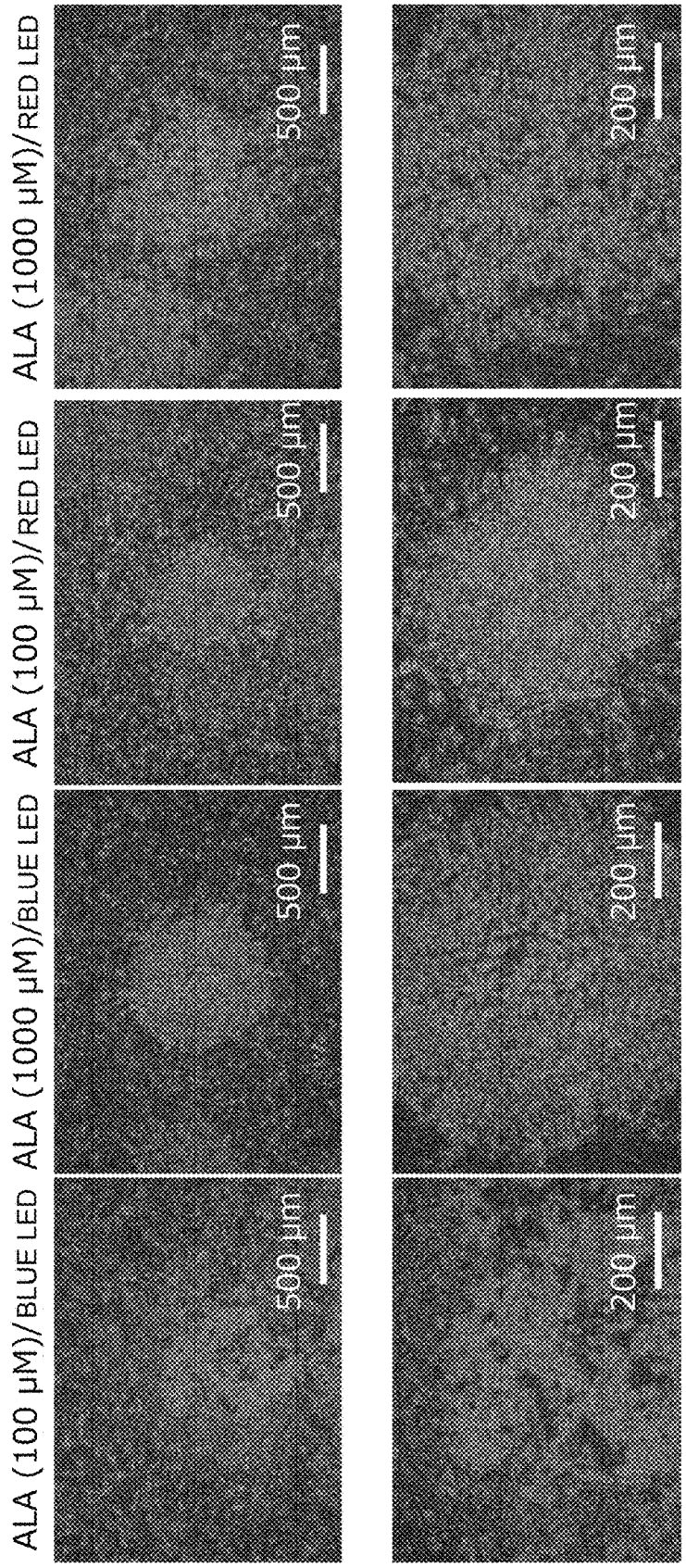

FIG.10
PHOTOIRRADIATION (BLUE/RED) (10-MINUTES) 4 HOURS AFTER ALA ADDITION
24 HOURS AFTER PROCESSING
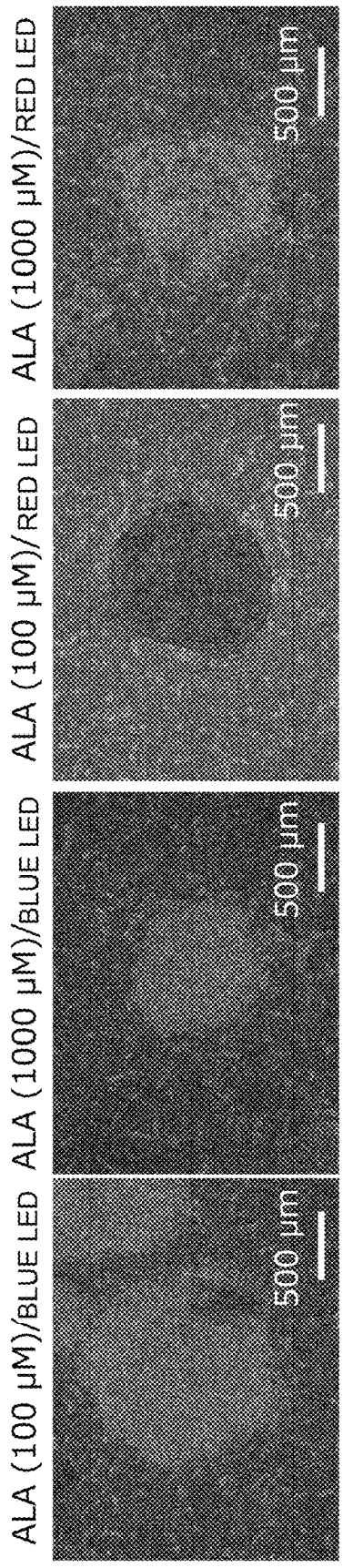
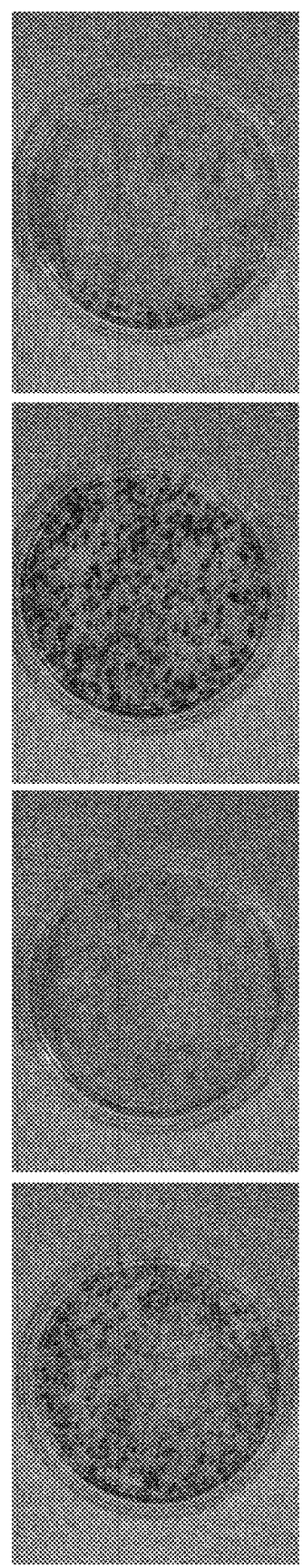

FIG.14

| ALA CONCENTRATION | 0 μM | | 250 μM | | 500 μM | |
|---|---|---|---|---|---|---|
| LED IRRADIATION TIME | 0 MINUTE | 0 MINUTE | 0 MINUTE | 10 MINUTES | 0 MINUTE | 10 MINUTES |
| HUMAN IPS CELL | NO CHANGE | NO CHANGE | NO CHANGE | THERE WERE MANY DEAD CELLS. THEY WERE SLIGHTLY EXFOLIATED. | NO CHANGE | THERE WERE MANY DEAD CELLS. THEY WERE SLIGHTLY EXFOLIATED. |
| NEURON ORIGINATED FROM HUMAN IPS CELL | NO CHANGE | NO CHANGE | NO CHANGE | NEURAL SPINES WERE SHORTEN. CELL ADHESION WAS CONFIRMED. THEY WERE SURVIVED. | NO CHANGE | NEURAL SPINES WERE SHORTEN. CELL ADHESION WAS CONFIRMED. THEY WERE SURVIVED. |

FIG. 15
(b) AFTER 500 MICRO-M ALA EXPOSURE
10-MINUTE IRRADIATION
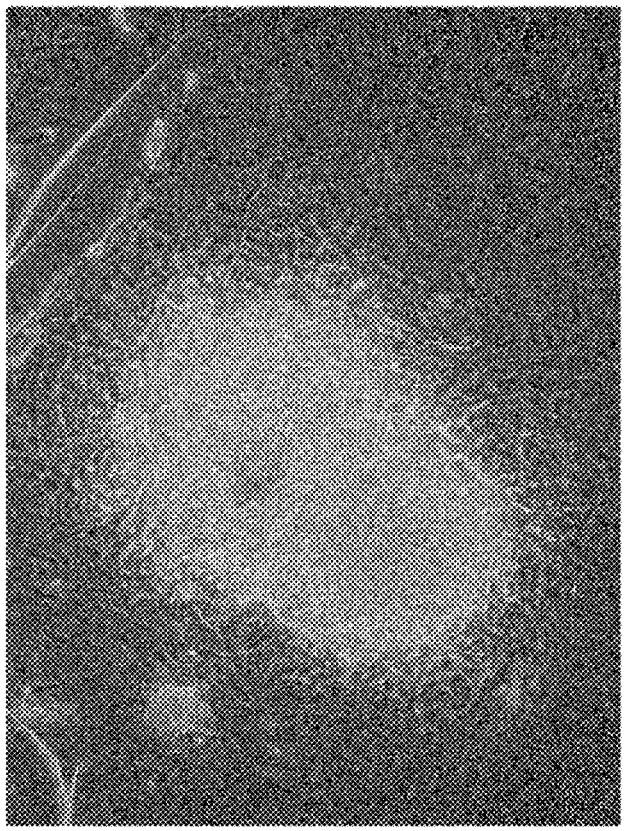
(a) BEFORE 500 MICRO-M ALA EXPOSURE

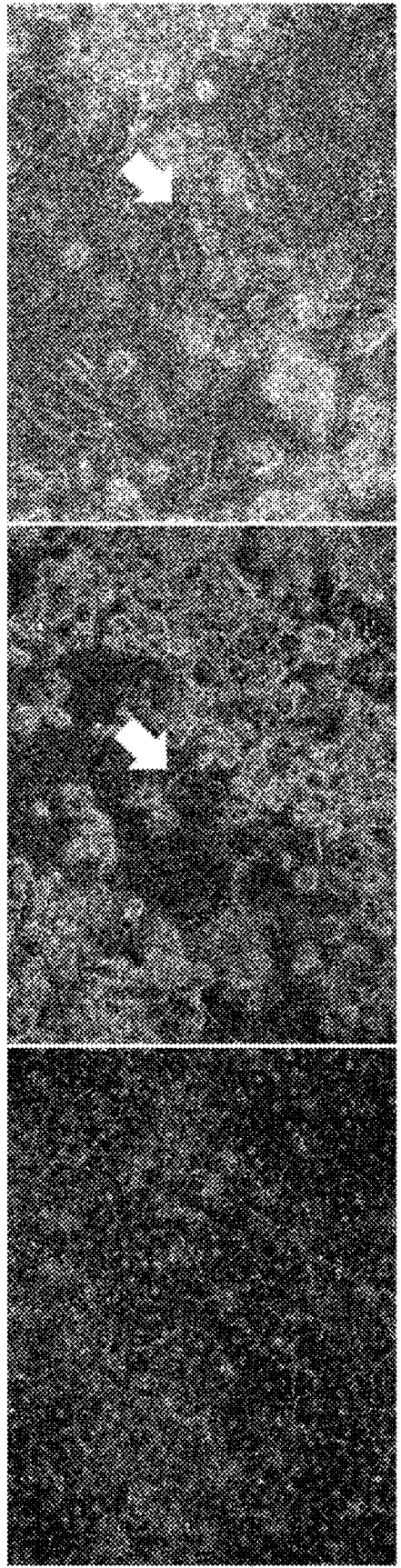

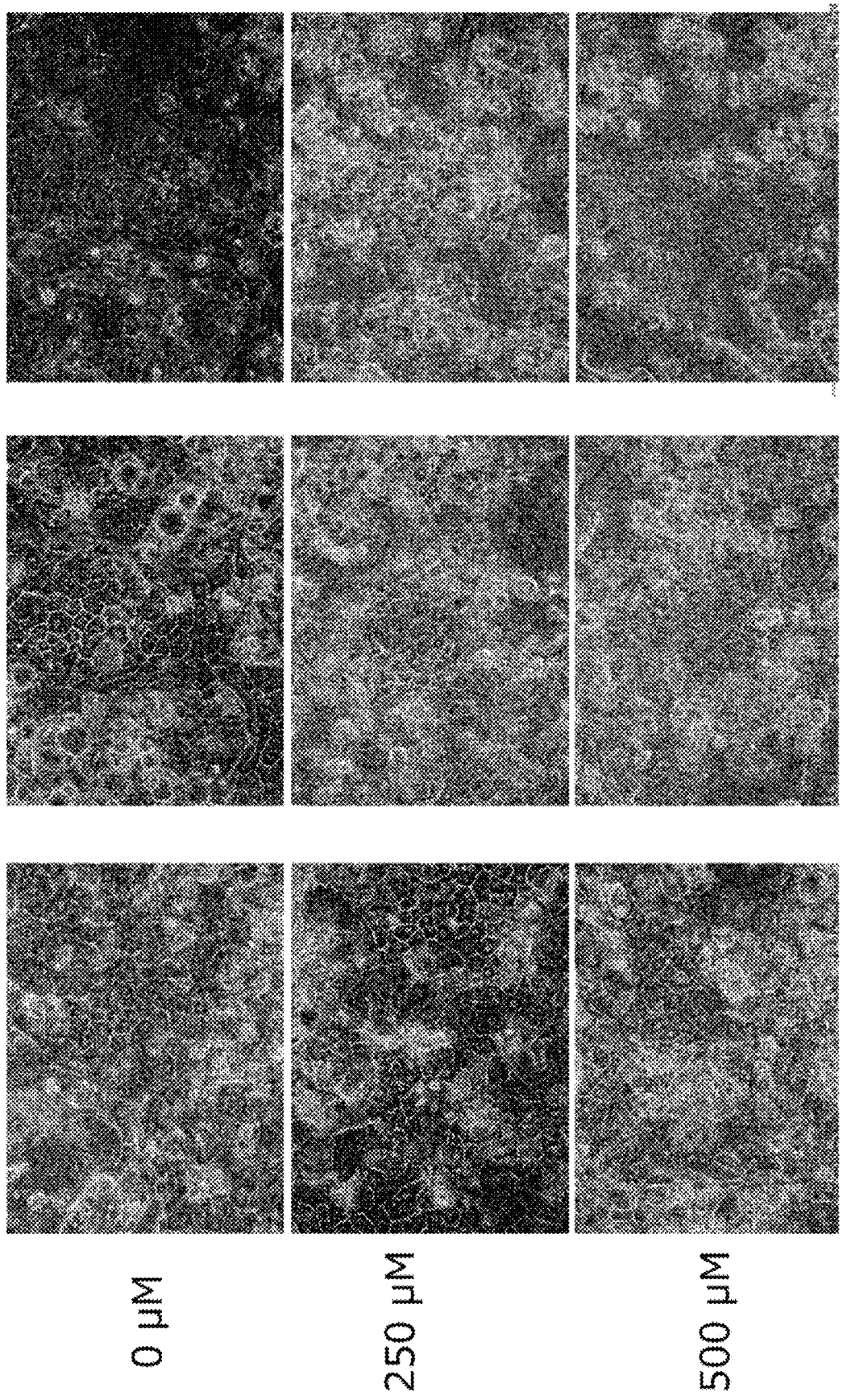

METHOD OF REMOVING PLURIPOTENT CELLS FROM CULTURE

FIELD OF THE INVENTION

The present invention relates to a stem cell removing method, a differentiated cell protective method, and culture medium composition, and, especially, it is related with a stem cell removing method, a differentiated cell protective method, and culture medium composition when making a pluripotent stem cell differentiate.

BACKGROUND OF THE INVENTION

An ES cell (Embryonic Stem Cells, ESCs) or an induced pluripotent stem cell (Induced Pluripotent Stem Cells, iPSCs) is a kind of a cell called a pluripotent stem cell (Pluripotent Stem Cell), and it is in an undifferentiated state and has capability where differentiation induction to the cells of all three germ layers is possible. Therefore, using a human pluripotent stem cell for a regenerative medicine of various diseases is expected, potentially.

When using the pluripotent stem cell for regenerative medicine, it is necessary to transplant to the living body in a state where differentiation induction has performed to cell groups, such as a specific cell, a tissue, or an internal organ.

For example, as refer to patent documents 1, it is disclosed a manufacturing method of a nerve cell sheet having a nerve cell layer formed of a nerve cell performed axis cylinder expansion including the steps of: culturing a nerve cell sheet having the lamina ganglionaris formed of the cultured nerve cell which performed axis cylinder expansion and a precursor cell in culture solution including a Sonic hedgehog inhibitor and a differentiation inducer, and inducing nerve cell from the precursor cell; and culturing a nerve cell in culture solution including at least one of SDF 1 (Stromal cells-derived factor-1) and MCP-1 (Monocyte chemoattractant propein-1), axis cylinder expansion of a nerve cell is induced, and obtaining the nerve cell layer formed of the cultured nerve cell performed axis cylinder expansion.

PRIOR ART DOCUMENT

Patent Documents

[Patent documents 1] JP2014-23457A

SUMMARY OF THE INVENTION

Problem(s) to be Solved by the Invention

However, if a pluripotent stem cell having an undifferentiated state is mixed in a cell group performed differentiation induction as like the technology of patent documents 1, since teratoma (teratoid tumor) occurs in vivo, it needs to be selected only the differentiated cell. Also, in case that differentiation induction of the somatic stem cell with the capability to differentiate to a specific cell line is performed and the somatic cell is manufactured, if the undifferentiated somatic stem cell remained, it might become causes, such as other tumors (Hereinafter, various stem cells including a pluripotent stem cell and a somatic stem cell are just called as a "stem cell".). Therefore, it is anxious for technology of efficiently-removing the stem cell from the cell group performed differentiation induction.

The present invention is accomplished in view of such a situation, and an object of the present invention is to solve the above-mentioned problem.

Means for Solving the Problem

A stem cell removing method of the present invention includes the steps of: cultivating a cell group including a stem cell and a somatic cell performed differentiation induction from the stem cell in culture medium composition including photosensitizer; irradiating with light of a specific wavelength to the cell group cultivated in the culture medium composition including the photosensitizer; and removing the stem cell from the cell group.

The stem cell removing method of the present invention is, wherein the stem cell is a pluripotent stem cell or a somatic stem cell; and the pluripotent stem cell includes an ES cell (Embryonic Stem Cell) or an iPS cell (induced Pluripotent Stem Cell), and the somatic stem cell includes anyone of a germ stem cell, a productive cell, a pluripotent stem cell and a stem cell having unipotency.

The stem cell removing method of the present invention is, wherein the photosensitizer is aminolevulinic acid (Amino Levulinic Acid), a derivative thereof, or a salt thereof.

The stem cell removing method of the present invention is, wherein concentration of the aminolevulinic acid, the derivative thereof, or the salt thereof is 10 micro-M to 2000 micro-M.

The stem cell removing method of the present invention is, wherein time until photoirradiation after adding the aminolevulinic acid, the derivative thereof, or the salt thereof is 4 hours or more.

The stem cell removing method of the present invention is, wherein wavelength of the light of the specific wavelength is 400 nm to 750 nm, the irradiation intensity is 1 $mW/cm^2$ to 200 $mW/cm^2$, and the irradiation time is 1 minute to 240 minutes.

A differentiated cell protective method of the present invention includes a step of protecting the somatic cell performed the differentiation induction when being removed by the stem cell removing method.

The differentiated cell protective method of the present invention is, wherein protected somatic cell is a mesoblast system cell.

The differentiated cell protective method of the present invention is, wherein protected somatic cell is an ectoderm system cell.

The differentiated cell protective method of the present invention is, wherein protected somatic cell is an endoderm system cell.

A culture medium composition of the present invention includes: a medium component for cultivating a cell group including a stem cell and a somatic cell performed differentiation induction from the stem cell; and photosensitizer.

The culture medium composition of the present invention is, wherein removes the stem cell when irradiating with light of a specific wavelength.

The culture medium composition of the present invention is, wherein protects the somatic cell performed differentiation induction when irradiating with the light of the specific wavelength.

The culture medium composition of the present invention is, wherein the stem cell is a pluripotent stem cell or a somatic stem cell, the pluripotent stem cell includes an ES cell (Embryonic Stem Cell) or an iPS cell (induced Pluripotent Stem Cell), and the somatic stem cell is a cell having pluripotency and self-replication ability.

The culture medium composition of the present invention is, wherein the somatic cell performed differentiation induction from the stem cell includes any one of the group consisting of a mesoblast system cell, an ectoderm system cell, and an endoderm system cell.

The culture medium composition of the present invention is, further includes a growth factor component that performs differentiation induction of the somatic cell from the stem cell.

The culture medium composition of the present invention is, wherein the medium component includes nutritional component for giving nutritive substance to a cell.

The culture medium composition of the present invention is, wherein the medium component includes a buffer component for keeping environment under cultivation constant.

The Culture medium composition of the present invention is, wherein the medium component includes a growth promotion component that promotes growth of the somatic cell.

The culture medium composition of the present invention is, wherein the photosensitizer is aminolevulinic acid (Amino Levulinic Acid), a derivative thereof, or a salt thereof.

The culture medium composition of the present invention is, wherein concentration of the aminolevulinic acid, the derivative thereof, or the salt thereof is 10 micro-M to 2000 micro-M.

The culture medium composition of the present invention is, wherein time until photoirradiation is performed after adding the aminolevulinic acid, derivative thereof, or salt thereof is 4 hours or more.

The culture medium composition of the present invention is, wherein wavelength of the light of the specific wavelength is 400 nm to 750 nm, the irradiation intensity is 1 mW/cm$^2$ to 200 mW/cm$^2$, and the irradiation time is 1 minute to 240 minutes.

Effect of the Invention

According to the present invention, technology can be provided that, by irradiating light of a specific wavelength to a cell group cultivated by culture medium composition including photosensitizer, a stem cell is easily removed from a cell group including a somatic cell performed differentiation induction and the stem cell.

BRIEF DESCRIPTION OF THE DRAWINGS

FIG. 7 is a photograph showing the iPS cell after 24 hours after performing ALA and/or SFC addition and irradiating with red LED in evaluation of the operation of ALA-PDT on the iPS cell according to Example 1 of the present invention.

FIG. 8 is a photograph showing expression of ALP investigated by a kit about the result in FIG. 7 of Example 1 of the present invention.

FIG. 9 is a photograph showing the iPS cell after 24 hours after performing ALA addition and irradiating with blue LED or red LED in comparison of the operation with the wavelength of the photoirradiation of ALA-PDT for the iPS cell according to Example 1 of the present invention.

FIG. 10 is a photograph showing expression of ALP investigated by the kit about the result in FIG. 9 of Example 1 of the present invention.

FIG. 14 is a table figure collecting the result of FIG. 13 in Example 1 of the present invention.

FIG. 15 is a photograph showing a cardiac muscle cell performed differentiation induction in the iPS cell in evaluation of an operation of ALA-PDT on the cardiac muscle cell originated from the iPS cell according to Example 1 of the present invention.

FIG. 17 is a photograph of a hepatic cells performed differentiation induction in the iPS cell in evaluation of an operation of ALA-PDT on the hepatic cells originated from the iPS cell according to Example 2 of the present invention.

FIG. 18 is a photograph of the hepatic cells performed differentiation induction in the iPS cell in evaluation of an operation of ALA-PDT on the hepatic cells originated from the iPS cell according to Example 2 of the present invention.

MODE FOR CARRYING OUT THE INVENTION

Embodiment

Figure 1:
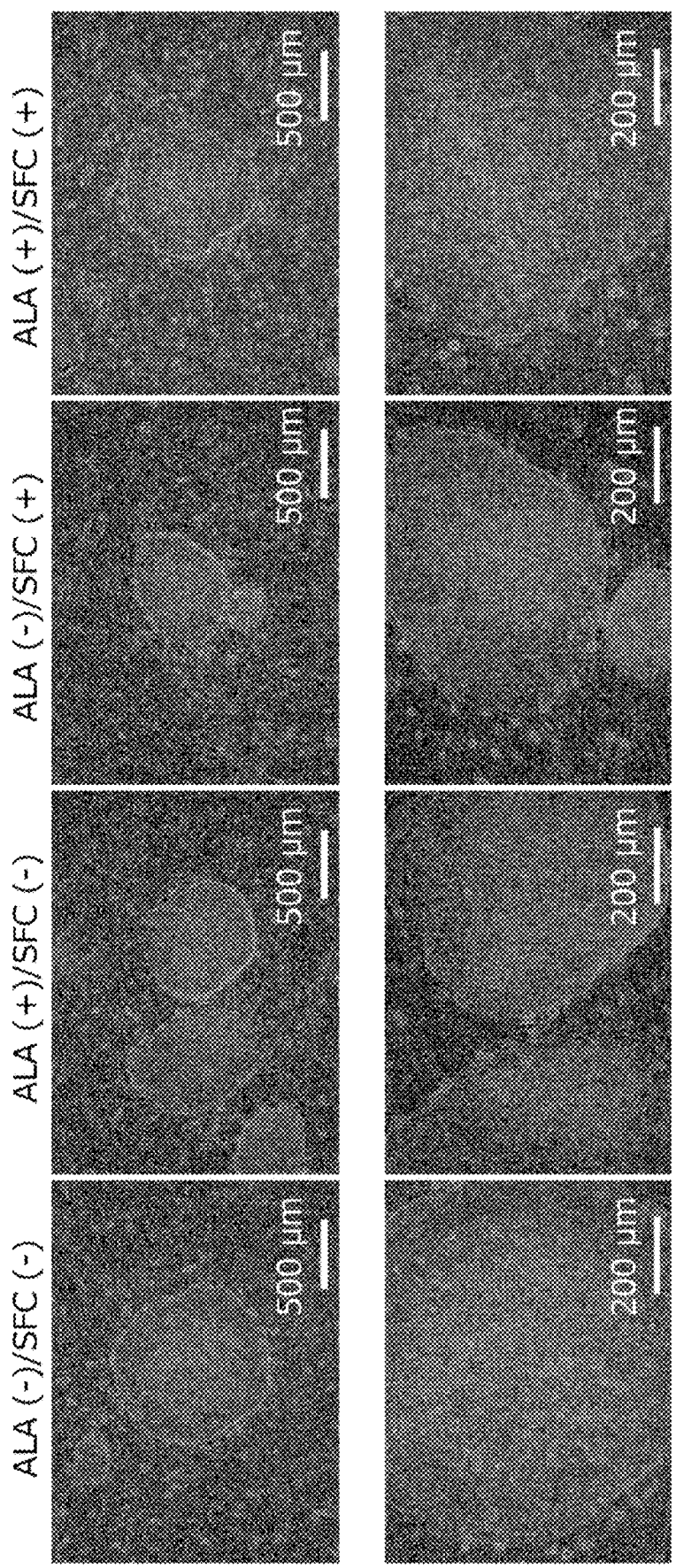
FIG. 1 is a photograph showing an iPS cell at time of addition (0 hour) in evaluation of an operation of ALA on an iPS cell according to Example 1 of the present invention.

The inventors have experimented wholeheartedly in order to realize a method of removing a stem cell having an undifferentiated state from a cell group including the stem cell and a somatic cell performed differentiation induction in the stem cell, easily. Then, we found that, in a PhotoDynamic therapy (hereinafter, it is referred as "PDT".) by using photosensitizer as like Amino Levulinic Acid (hereinafter, it calls "ALA". Also, hereinafter, PDT by using ALA is called "ALA-PDT".), although the stem cell becomes photosensitized, the somatic cell performed differentiation induction does not become photosensitized, easily. In other words, the degree of photosensitization is different between the stem cell and the somatic cell performed differentiation induction. These inventors further advance the experiment, by applying ALA-PDT to the respective pluripotent stem cell, after undifferentiated stem cells are easily removed from the cell group performed differentiation induction, technique of protecting the somatic cell performed differentiation induction is established, and it comes to complete the stem cell removing method, the cytoprotection method, and culture medium composition in the present invention.

In addition, in the present embodiment, the removal of a stem cell is realized with a means of induction of cell death, exfoliation and separation, a division-stop of a cell, not-maintaining of a cell to an undifferentiated state, prevention of undifferentiated-state maintenance capability, induction to a differentiational state, elimination of teratoma forming ability, or the like. Also, in the present embodiment, photosensitization means that, when it is irradiated with light of a specific wavelength by PDT which uses photosensitizer, cell death, the exfoliation and separation, the division-stop of a cell, or the ability of a cell changes. The change of the ability of this cell, or the like, includes prevention of undifferentiated maintenance ability, induction to a differentiational state, change of teratoma forming ability, or the like.

Hereinafter, as an embodiment, it is written the details of the stem cell removing method, the cytoprotection method, and culture medium composition in the present invention.

As explained in detail, the stem cell removed in the present embodiment includes a pluripotent stem cell and a somatic stem cell, especially.

In these, the pluripotent stem cell in the present embodiment includes a stem cell having pluripotency that can differentiate in various cells of living organism, such as the primates including *Homo sapiens*, the mammals other than the primates, and other vertebrates. Also, the pluripotent stem cell in the present embodiment preferably has a property that a passage is possible, a state of not-progressing differentiation is maintained even when it is passaged, a karyotype, or the like, is hard to be changed, or an epigenetic phenotype is hard to be changed. Also, in connection with this, the pluripotent stem cell in the present embodiment preferably has sufficient proliferating capability in vitro or in vivo. As an example of the pluripotent stem cell in the present embodiment having such property is an embryonic stem cell (ES cell), an induced pluripotent stem cell (iPS cell), a stem cell having pluripotency artificially-generated or selected, or the like, are exemplified. The artificially-generated pluripotent stem cell may be a pluripotent stem cell generated by reprogramming a somatic cell by using various vectors, such as a retrovirus, adenovirus, a plasmid, or the like, including a specific gene, RNA, a low molecular weight compound, or the like.

In addition, for the pluripotent stem cell in the present embodiment, although it does not always necessarily to have a cell having a pluripotency as similar to totipotency, it is also possible to use a "naive" cell, which has more pluripotency than a common pluripotency. Also, in the pluripotent stem cell in the present embodiment, an addition, modification, and/or deletion, of a gene in a chromosome, addition of gene, or the like, by various vectors or an artificial chromosome, change of epigenetic control, addition of an artificial genetic material, such as PNA, or the like, and/or other genetic modifications may be performed.

Also, the somatic stem cell in the present embodiment includes either a germ stem cell, a reproductive cell, a pluripotent stem cell and a stem cell having unipotency.

As an example of the pluripotent stem cell and the stem cell having unipotency, a hematopoietic stem cell, an epidermal stem cells, an intestinal tissue stem cell, a mesenchymal stem cell, and a neural stem cell are included in such somatic stem cells. In addition, it may be somatic cells other than embryonic stem cells, and it may be a cell having pluripotency and self-replication ability, simultaneously. Also, the somatic stem cell in the present embodiment may be a stem cell of a specific tissue, or the like.

Also, the somatic stem cell in the present embodiment may be a stem cell that a somatic cell generated by the reprogramming of the somatic cell, directly, by various vector(s), a RNA, a low molecular weight compound, or the like.

Also, the somatic cell protected in the present embodiment at the time of removal of the stem cell is the somatic cell performed differentiation induction from the stem cell.

Such the somatic cell includes a cell performed differentiation induction to a specific stage, and a somatic cell that have reached the final stage of differentiation by adding a growth factor component (as described later), which is a specific factor for performing differentiation induction to the above-mentioned pluripotent stem cell and the somatic stem cell under a specific culture condition.

Also, the somatic cell in the present embodiment may be a cell where a specific character being able to be differentiated to a cell of a specific series is fixed.

Also, the somatic cell performed differentiation induction to the specific stage in the present embodiment includes a cell of a mesoblast, an ectoderm, or an endoderm. The cell of mesoblast, an ectoderm, or an endoderm includes a cell, various precursor cells, or the like, which is differentiated to express a specific genetic marker. In this case, the somatic cell in the present embodiment may be a cell performed differentiation induction to a specific type of series, which is selected in a form of a colony, or the like, by various marker(s), by visual inspection, or the like. Also, the somatic cells in the present embodiment may be a mixed cell mass, a tissue, an organ, or the like (hereinafter, it is called "tissue, or the like".), including various somatic cells performed differentiation induction. An example of the tissue, or the like, may be a tissue having three-dimensional structure, such as a brain tissue, an optic vesicle, an optic cup, a lens vesicle, and a hepatic lobule, a skeletal muscle tissue performed cell fusion, various cell sheet(s), a tissue laminated the cell by 3D printer, a tissue held on a carrier, or the like. Also, a structure, such as a blood vessel, may be formed in the tissue, or the like. Also, from the tissue, or the like, as described later, only a specific type of somatic cell may be sorted based on the presence or absence, or the degree of photosensitization by ALA-PDT.

Also, in the present embodiment, for example, a cardiac muscle cell is mentioned as an example of a mesoblast cell. However, it is not limited to this, and another mesenchymal cell(s) may be used. Also, as an example of the other mesoblast cell(s), a cell, such as a bone, a connective tissue, a muscle, blood, a germinal gland, or the like, may be listed.

Also, in the present embodiment, for example, a neuron is listed as an example of an ectoderm cell. Also, as an example ectoderm cell, a cell, such as a central nerve, a peripheral nerve, a neuron, an axon, a myelin sheath, a skin, a cornea, a retina, an inner ear, an outer ear, or the like, may be listed.

Also, in the present embodiment, for example, a hepatic cell is listed as an example of an endoderm cell. Also, as a specific example of endodermal cell, other digestive or respiratory cell is listed.

Also, the photosensitizer in the present embodiment is the photosensitizer for PDT that absorbs light of a specific wavelength and generates fluorescence and/or active oxygen.

In the present embodiment, ALA is suitably used as an example of such photosensitizer. The ALA can be used ALA itself, derivative(s) thereof (hereinafter, is called "ALA(s)"), or salt(s) thereof. ALA is a kind of amino acid and generates neither fluorescence nor active oxygen by the photoirradiation of visible light in itself. Also, ALA has little cytotoxicity and its safety is high. However, after introducing into a cell, ALA is metabolized to the protoporphyrin, which is a photosensitization substance, and acts as photosensitizer.

ALA and a derivative thereof is shown as following formula (I). In formula (I), R1 represents a hydrogen atom or an acyl group, and R2 represents a hydrogen atom, a straight chain or a branched alkyl group, a cycloalkyl group, an aryl group, or an aralkyl group.

[Formula 1]

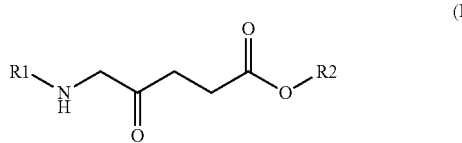

(I)

As ALA in the present embodiment, ALA or a salt thereof in which both R1 and R2 in formula (I) are hydrogen atoms is suitably exemplified. ALA is a kind of the amino acid called delta-aminolevulinic acid.

Also, as ALA derivative(s), compound(s) other than 5-ALA where R1 in formula (I) is a hydrogen atom or an acyl group, R2 in formula (I) is a hydrogen atom, a straight chain or a branched alkyl group, a cycloalkyl group, an aryl group, or an aralkyl group are listed.

As the acyl group in formula (I), a straight or branched chain alkanoyl group having 1 to 8 carbon atoms, such as formyl, acetyl, propionyl, butyryl, isobutyryl, valeryl, isovaleryl, pivaloyl, hexanoil, octanoyl, benzyl carbonyl group, or the like, and an aroyl group having 7 to 14 carbon atoms such as benzoyl, 1-naphthoyl and 2-naphthoyl group, or the like is listed.

As the alkyl group in formula (I), an alkyl group of a straight or branched chain having 1 to 8 carbon atoms, such as methyl, ethyl, propyl, isopropyl, butyl, isobutyl, sec-butyl, tert-butyl, pentyl, isopentyl, neopentyl, hexyl, heptyl, octyl, or the like are listed.

As the cycloalkyl group in formula (I), a cycloalkyl group having 3 to 8 carbon atoms that may be saturated bond or may be partially-unsaturated bond, such as a cyclo propyl, cyclo butyl, cyclopentyl, cyclohexyl, cycloheptyl, cyclo octyl, cyclo dodecyl, 1-cyclohexenyl group, or the like is listed.

As an aryl group in formula (I), an aryl group having 6 to 14 carbon atoms, such as phenyl, naphthyl, anthryl, phenanthryl, or the like is listed.

As an aralkyl group in formula (I), the aryl part may be the same exemplification as the above-mentioned aryl group. Also, the alkyl part may be the same exemplification as the above-mentioned alkyl group. In detail, the aralkyl group having 7 to 15 carbon atoms, such as benzyl, phenetyl, phenylpropyl, phenylbutyl, benzhydryl, trityl, naphthylmethyl, naphthylethyl group, or the like, is listed.

As an above-mentioned ALA derivative, a compound where R1 is formyl, acetyl, propionyl, butyryl, or the like, or a compound where R2 is methyl, ethyl, propyl, butyl, pentyl, or the like, is preferred. Also, the above combination of R1 and R2 may be preferably-exemplified as a combination of formyl and methyl, acetyl and methyl, propionyl and methyl, butyryl and methyl, formyl and ethyl, acetyl and ethyl, propionyl and ethyl, butyryl and ethyl, or the like.

The ALA(s) may act as an active ingredient in vivo in a state of ALA of formula (I) or a derivative thereof, and, according to a form prescribed for a patient, it can be administered as various salts to increase solubility, an ester, or a prodrug (precursors), which is decomposed by enzymes in vivo. For example, as the salt of ALA and the derivative thereof, acid addition salt, metal salt, ammonium salt, organic amine addition salt, or the like, which is pharmacologically-permitted, can be listed. As the acid addition salt, for example, an inorganic acid salt, such as hydrochloride, hydrobromate, hydriodic acid salt, a phosphate, a nitrate, a sulfate, or the like, or an organic acid addition salt, such as formate, acetate, propionate, toluenesulfonic acid salt, succinate, oxalate, lactate, tartrate, glycolate, methanesulfonic acid salt, butyrate, valerate, citrate, fumarate, maleate, malate, or the like, may be exemplified. As the metal salt, a metal salt of an alkali metal salt, such as lithium salt, sodium salt, potassium salt, or the like, alkaline-earth-metals salt, such as magnesium and calcium salt, or the like, other metal salt, such as aluminum and zinc salt may be exemplified. As the ammonium salt, alkyl ammonium salt, such as ammonium salt, tetramethylammonium salt, or the like, may be exemplified. As the organic amine salt, a salt, such as triethylamine salt, piperidine salt, morpholine salt, toluidine salt, or the like, may be exemplified. In addition, these salts can also be used as solution at the time of use.

The preferable above-mentioned ALA(s) is ALA, various ester thereof, such as ALA methyl ester, ALA ethyl ester, ALA propyl ester, ALA butylester, ALA pentyl ester, or the like, or hydrochloride, a phosphate, or sulfate thereof. In these, ALA hydrochloride and an ALA phosphate may be preferably-exemplified, particularly.

Also, ALA(s) may be a hydrate or a solvate, and either one of these may be used alone or two or more of them may be combined, appropriately. Also, ALA(s) may be manufactured by a method of chemical synthesis, production by a microorganism, or production by an enzyme.

Also, when ALA(s) is prepared as solution, in order to prevent decomposition of ALA(s), it is necessary to take care that the solution does not become alkaline. When becoming alkalinity, decomposition can be prevented by removing oxygen.

Also, as photosensitizer in the present embodiment, other than ALA(s) or salt thereof, any photosensitizer capable of absorbing visible light, emitting fluorescence, and/or capable of generating active oxygen may be used. Especially in the present embodiment, a tetrapyrrole-based compound may be preferably-exemplified. As a specific example, photofrin, rezafurin, protoporphyrin IX, Foscan, chlorin, uroporphyrin I, uroporphyrin III, hepta-carboxyl porphyrin I, hepta-carboxyl porphyrin III, hexa-carboxyl porphyrin I, hexa-carboxyl porphyrin III, penta-carboxyl porphyrin I, penta-carboxyl porphyrin III, coproporphyrin I, coproporphyrin III, isocoproporphyrin, halodroporphyrin, isohalderoporphyrin, hematoporphyrin, mesoporphyrin, etioporphyrin, pyroporphyrin, deuteroporphyrin IX, etioporphyrin, ATXs-10, or the like may be listed. Also, it is preferable to use dosage equivalent to the amount effective for ALA-PDT.

Also, as photosensitizer in the present embodiment, the compound that increases the effect of ALA-PDT, such as sodium ferrous citrate (hereinafter, it is called "SFC".), may be added to ALA.

In the present embodiment, when it is added to a culture medium composition as described later as photosensitizer and is used in a stem cell removing method or a differentiated cell protective method, it is preferred for the concentration of ALA(s) or a salt thereof is 10 micro-M to 2000 micro-M, and more preferred is 100 micro-M to 1500 micro-M. When the concentration of ALA(s) or a salt thereof is less than 10 micro-M, the rate of removing a pluripotent stem cell or a somatic stem cell by ALA-PDT is not sufficient. Also, even when the concentration of ALA is equal or greater than 2000 micro-M, the effect of removing a pluripotent stem cell or a somatic stem cell by ALA-PDT does not change.

Also, in the present embodiment, the concentration of ALA(s) or a salt thereof can be appropriately-adjusted depending on type of pluripotent stem cell or somatic stem cell, type of somatic cell performed differentiation induction, culture condition, light irradiation condition of specific wavelength, or the like. For example, as shown in the after-mentioned example, when ALA(s) or salt thereof of 250 micro-M to 500 micro-M is introduced and is performed PDT for a cell group including the neuron performed differentiation induction from the iPS cell, it is possible to protect the neuron performed differentiation induction while removing 60% or more pluripotent stem cells or somatic stem cells in 24 hours. On the other hand, in case of a colony including the cardiac muscle cell performed differentiation induction from the iPS cell, when PDT is performed at a concentration of 500 micro-M ALA(s) or a salt thereof, pulsation may be lost, and a colony may also collapse. Therefore, for example, it is preferred to perform PDT by introducing about a concentration of 100 to 400 micro-M ALA(s) or a salt thereof. Conversely, a configuration is also possible that, by utilizing the effect that PDT on a specific concentration of ALA(s) or a salt thereof varies depending on somatic cell type, for example, from a mixed cell mass where a pluripotent stem cell or a somatic stem cell, and a neuron and a muscle cell are included, by ALA-PDT at the concentration of 500 micro-M to 1500 micro-M ALA(s) or a salt thereof, only a neuron can be protected and be obtained, and the other cell can be removed.

Also, in the present embodiment, it is preferable that the time until photoirradiation is performed after adding ALA(s) or a salt thereof is 4 hours or more, and more 24 hours or more is more preferable.

In detail, when PDT is performed after introducing ALA(s) or a salt thereof and 4 hours or more is passed as compared with not-performed ALA introduction as like this, it becomes possible to remove more undifferentiated pluripotent stem cells or somatic stem cells. Furthermore, when PDT is performed after introducing ALA(s) or a salt thereof and 24 hours or more is passed, it is possible to protect the cell performed differentiation induction with removing pluripotent stem cells or somatic stem cells, which they become about 7%. In this case, as shown in the following Example 2, it obtains sufficient effect with concentration of ALA(s) or a salt thereof at 250 micro-M-to 1000 micro-M.

Also, in the present embodiment, it is preferred that the wavelength of the light of the specific wavelength irradiated is 400 nm to 750 nm, irradiation intensity is 1 mW/cm$^2$ to 200 mW/cm$^2$, and irradiation time is 1 minute to 240 minutes. More suitably, the irradiation intensity of the light of the specific wavelength is 10 mW/cm$^2$ to 20 mW/cm$^2$, and the irradiation time is 5 minutes to 20 minutes.

More specifically, light of the specific wavelength used for ALA-PDT in the present embodiment, as the wavelength of ultraviolet light to visible light to a near infrared, it is usable in light with a wavelength of 400 to 750 nm. The is a reason that a damage is serious to DNA, or the like, for the somatic cell performed differentiation induction in an ultraviolet light range where the wavelength is less than 400 nm, and it deviates from the optical absorption region of the protoporphyrin metabolized from ALA within the cell in the infrared area range where it is 750 nm or more.

Also, as the wavelength of the light of the specific wavelength in the present embodiment, the blue light of 430 nm to 480 nm and red light of 580 to 600 nm in visible light can be suitably-used, particularly, because the effect that protects the somatic cell performed differentiation induction is high.

Also, as the irradiation intensity of the light of the specific wavelength in the present embodiment, it is preferred about 1 mW/cm$^2$ to 200 mW/cm$^2$. More suitably, the irradiation intensity of the light of the specific wavelength is about 10 mW/cm$^2$ to 20 mW/cm$^2$. In this case, irradiation may be performed by using the irradiation equipment of general LED (Light Emitting Diode), the irradiation equipment by using laser (not shown), or the like.

Also, it is preferred that the irradiation time of the light of the specific wavelength in the present embodiment may be about 1 minute to 240 minutes. More suitably, the irradiation time of the light of the specific wavelength is about 5 minutes to 30 minutes, and more suitably about 10 minutes to 20 minutes. If irradiation time is shorter than 1 minute, a pluripotent stem cell or a somatic stem cell cannot sufficiently be removed from a cell group including the somatic cell performed differentiation induction with the pluripotent stem cell or the somatic stem cell. Also, if longer than 240 minutes, the somatic cell being to cell death is increased. Also, as the present inventors' investigation, it is understood that the pluripotent stem cells or the somatic stem cells has lower PDT sensitivity than cancer cells by a preliminary experiment. Therefore, in the present embodiment, irradiation time for removing the stem cell capable photosensitivity by being added photosensitizer is preferred, for example, 10 minutes or more, which is time longer than PDT for various cancer cells, or the like. Also, in order to cut the damage by the photoirradiation to the somatic cell, suitable irradiation time is selected with a cell type. In this case, it is preferred that it may be longer than 30 minutes in a fibroblast, and, conversely, it is preferred that it may be less than 30 minutes and, especially, less than 20 minutes in a neuron. Thereby, even if a cell cancerized in the course of differentiation induction is included, it is removed, and, furthermore, while an undifferentiated pluripotent stem cell or a somatic stem cell removes, it also becomes possible to protect the somatic cell performed differentiation induction.

In addition, also about the wavelength of the light irradiated and irradiation time by the PDT, can be adjusted, suitably, by a condition, such as the type of the pluripotent stem cell or the somatic stem cell, the type of somatic cell performed differentiation induction, the culture condition, the concentration of ALA(s) or the salt thereof, or the like.

Also, the culture medium composition in the present embodiment includes a stem cell, a medium component for cultivating a cell group including a somatic cell performed differentiation induction from the stem cell, and photosensitizer.

For example, the medium component in the present embodiment can use culture medium, or the like, which include a specific component specialized in the stem cell or the somatic cell as a culture medium for the stem cell or the somatic cells.

Also, the medium component of the culture medium composition in the present embodiment includes a growth factor component for performing differentiation induction of a somatic cell from a stem cell, a buffer component for keeping cultivation environment constant, a nutritional component for giving nutritive substance to a cell, and the growth promotion component for promoting growth of a somatic cell performed differentiation induction.

In these, the growth factor component included in the medium component in the present embodiment, for example, as a component for performing differentiation induction to a cardiac muscle cell, low molecular weight component, such as KY02111 (WNT pathway inhibitor, CAS Number: 1118807-13-8) or BIO (GSK-3 inhibitor, CAS Number: 667463-62-9) may be used. Also, as a component for performing differentiation induction to a neuron, DAPT (gamma-Secretase Inhibitor IX), retinoic acid, LIF (leukemia inhibitory factor), CNTF (ciliary neurotrophic factor), and NOGGIN, or the like, may be used. Also, as a component for performing differentiation induction to a hepatic cell, Activin A may be added, and gene products of SOX17 and HEX, or the like, may be added corresponding to a type of each somatic cell. In addition, for the growth factor component, in order to perform differentiation induction to the target somatic cell, various peptide(s), a protein, a micro RNA, a viral vector, a plasmid vector, or the like, other than a low molecular weight component may be included. In case of the viral vector, the plasmid vector, or the like, in their sequences, a mRNA, a ribozyme, RNAi, or the like, for a gene corresponding to the somatic cell to perform differentiation induction may be included.

Also, as for the nutritional component included in the medium component in the present embodiment, various serum, a serum replacement, an amino acid, a vitamin, an antioxidant, an antibiotic, a collagen precursor, a trace-mineral ion and complex, various salt(s), or the like, may be added and used. In these, the culture medium, which various serum replacement(s) is included, may be used for a culture condition not-included any component originated from different species (Xeno-Free, XF or Animal. Component-Free, ACF). In addition, various serum may be added to the medium component in the present embodiment.

Also, as for the buffer component included in the medium component of the present embodiment, in order to maintain pH of a medium component within $CO_2$ incubator, sodium bicarbonate, a phosphate, HEPES (N'-2 Hydroxyet hylpiperazine-N'-2 ethanesulphonic acid), MOPS (3-Morpholino-propanesulfonic acid) and Tricine, or the like, is included. Also, in order to view pH of the buffer, phenol red (Phenol Red) may be added. Also, in addition, a component for maintaining the environment of the medium component may be added.

Also, as for the growth promotion component of the somatic cell included in the medium component in the present embodiment, a component that is a growth factor, such as FGF (Fibroblast growth factors), EGF (Epidermal Growth Factor), HGF (Hepatocyte growth factor), or the like may be added at the concentration corresponding to the type, or the like, for the stem cell to culture and the somatic cell performed differentiation induction.

In addition, another required component(s) may be added to the medium component in the present embodiment.

Also, as for the culture medium composition in the present embodiment, culturing a stem cell only with the medium component is performed, and then, when performing differentiation induction of the respective stem cell to a somatic cell, photosensitizer may be added. Also, contrary, the photosensitizer may be added before performing differentiation induction of the stem cell. Also, the time when the photosensitizer is added can be suitably-selected by a type of stem cell, a type of the somatic cell performed differentiation induction, a protocol of performing differentiation induction, a timing for adding ALA(s) or a salt thereof, a timing of irradiation of the light of the specific wavelength, or the like.

Also, when culturing the pluripotent stem cell or the somatic stem cell with the somatic cell performed differentiation induction in the present embodiment, in case of an adhesive cell, it may be cultivated on a plate for a cell culture, or the like, having feeder cell layer or having coated basement membrane matrices, such as collagen, or the like. Also, at the time of subculturing of these cells, cultured cells may be obtained and dissociated into single cells, and the medium component(s) may be added. Also, the reagent for stem cell separation including a protease, a chelating agent, or the like, can be used for dissociating into single cells. In addition, a case of a type of an adhesive pluripotent stem cell or an adhesive somatic cell, or a case of a pluripotent stem cell or a somatic cell that is a floating cell, such as blood systems, a passage may be performed without performing the dissociation process of a cell.

Also, in the present embodiment, the somatic cell removed the stem cell by ALA-PDT may be used for medical treatment, or the like, immediately, or it may be used for the medical treatment, or the like, after detecting the stem cell being remained or not by using various genetic markers, or the like. In this case, the somatic cells may be cultured for a specific period of time, or subcultured several times. For example, by cultivating the cell group after the ALA-PDT process about for 12 hours (overnight) to 48 hours, the stem cell is annihilated by oxidative stress, or the like, and the somatic cell can be recovered from the damage by ALA-PDT. Also, after that, the somatic cell may also be performed differentiation induction into a finally-differentiated cell. Also, a plurality of types of somatic cells may be mixed, and a tissue or an organ may be generated.

Also, as medical treatment, or the like, realizable with the stem cell removing method and the somatic cell protective method in the present embodiment, for example, in a case of the cardiac muscle cell, it can be injected into a heart having a disease, used for a treatment of transplantation of a cardiac muscle sheet or a cardiac muscle tissue, or the like. Also, in a case of the neuron, it is possible to use for the medical treatment for a disease of a brain as like Parkinson's disease or Alzheimer's disease, cerebral injury by an accident, cerebral infarction, a tumor, or the like, a spinal cord injury, other treatment for central nervous or peripheral nervous regeneration, or the like. Also, in a case of the hepatic cell, it is possible to use for the medical treatment of the improvement in a function of the liver by liver cirrhosis, liver cancer, or the like, it is possible to use by injection into the spleen or the abdominal cavity, transplant of the liver held by a carrier, or the like.

Also, for example, the organ manufactured by using the somatic cell with the stem cell removing method and somatic cell protective method in the present embodiment may be grown up and obtained with a technique of the xenotransplantation to a nude mouse, a genetically-modified pig, or the like, and it is also possible to use for transplantation to a human for a therapeutic purpose.

As configuring as described above, the following effects can be obtained.

In recent years, technology that differentiation induction of various kinds of somatic cells is performed from the pluripotent stem cell or the somatic stem cell and has especially-used them for regenerative medicine is under development, and it is necessary to secure safety.

Also, conventionally, as the method that supplies the photosensitizer making a cancer cell photosensitization, makes a photochemical reaction in a malignant tumor, and makes the tumor tissue necrose, PDT is advocated (for example, as refer to WO2013/005379, or the like). However, it is not known whether PDT can be used or not in order to remove a pluripotent stem cell or a somatic stem cell and to protect the somatic cell performed differentiation induction at the time.

On the other hand, in the stem cell removing method of the present embodiment, a cell group including a stem cell and a somatic cell performed differentiation induction is cultivated by culture medium composition including ALA(s) or salt thereof, the cultivated cell group is irradiated with the light of a specific wavelength, and the stem cell is removed from the cell group. Thereby, while removing the stem cell, which should not be remained at time of a transplantation, from the somatic cell performed differentiation induction from the stem cell, easily, it is possible to protect the target somatic cell performed differentiation induction.

Therefore, in the present embodiment, it becomes possible to provide the somatic cell performed differentiation induction that is usable for regenerative medicine, safely and effectively. Also, according to the present embodiment, only by adding ALA(s) or salt thereof, being cultivated, and being performed photoirradiation, the stem cell can be removed, and thus cost can also be reduced. Also, since ALA is an amino acid used for a food additive or a medical application, even if it remains, its safety is high, and it becomes usable for a medical application, easily.

In addition, the somatic cell obtained by the stem cell removing method and the somatic cell protective method in the present embodiment can be used purposes other than regenerative medicine, and, for example, it is usable to various purposes, such as an examination of medicinal side effects, a bioreactor, manufacture of an artificial organ, generating of a clone body, or the like.

Example 1

Then, the present invention is further explained with examples based on figures. However, the following examples do not limit the present invention.
[Experimental Material and Method]

Maintenance of Pluripotent Stem Cell

As a pluripotent stem cell line, a human iPS cell line (iPSC) established at ReproCELL Inc. and subcultured 50 times was used. For on-feeder cultivation, the cell line of the pluripotent stem cell was maintained on mouse embryonic fibroblast (MEF) feeder cell (RCHEFC003, ReproCELL Inc.) processed by mitomycin C in a 60-mm polystyrene plate (dish) coated by ReproCoat (ReproCELL Inc.) with culture medium for pluripotent stem cells (Primate ES cell medium, RCHEMD001, ReproCELL Inc.) as like the conventional technique. ReproCoat was coated by using on a plate at the concentration of 0.2 micro-g/cm$^2$ and allowing to keep it at 4 degree-Celsius, overnight.
(Somatic Cell Performed Differentiation Induction and Other Somatic Cells)

About the somatic cell performed differentiation induction from the pluripotent stem cell, ReproCardio 2 (RCESD008, ReproCELL Inc.), which is a cardiac muscle cell as an example of a mesoblast cell, ReproNeuro (RCESDN001, ReproCELL Inc.), which is a neuron as an example of an ectoderm cell, ReproHepato Type 1 (RCESDH001, ReproCELL Inc.), which is a hepatic cell as an example of an endoderm cell, were cultivated and used according to the attached protocol, respectively. In this case, the passage was performed and cultured until it extended axons enough for the neuron, until it became a cardiac muscle cell mass having pulsation for the cardiac muscle cells, and until it became to have three-dimensional structure for the hepatic cell, respectively.

Also, the commercial normal human dermal fibroblast (CA106K05a, Cell Applications Inc., HDF) was used for comparative example(s).

As for the medium component for maintenance, each cell is cultivated by using an attached culture medium for the cell according to the protocol written in the attached manual, respectively.
(Preparation Method of ALA Solution and SFC Solution)

34 mg of ALA hydrochloride (M. W.=167.6, SBI Pharmaceuticals Co., Ltd.) was weighed, and 1000 micro-L of PBS (−) (Wako Pure Chemical Industries Ltd.) were added. Thereby, 200 mM ALA solution was prepared. The solution of the prepared ALA hydrochloride (hereinafter, it is only called as "ALA solution") was stored on a freezer at −20 degree-C until use.

Also, the solution of SFC (Kanto Kagaku, Inc.) having equivalent concentration was prepared and stored.
(ALA-PDT)

(The following shows the quantity in a case of a 60-mm dish) ALA solution (200 mM) was picked out from the freezer, and it was dissolved on ice. 4 mL of culture medium for cultivating the pluripotent stem cell or the somatic cell performed differentiation induction was prepared. 20 micro-L of ALA solution (200 mM) was added. Thereby, it became the culture medium having 1 mM ALA. Then, it mixed by pipetting, the cell was picked out from 5% $CO_2$ incubator, the culture medium was removed by suction, or the like, and 4 mL of culture medium including ALA was added. In addition, the quantity of the ALA solution to add was adjusted with the concentration of ALA included in the culture medium. The cell was returned to 5% $CO_2$ incubator, and it cultivated 4 hours to the time specified by each experiment. The cell was picked out, and it irradiated with the light of the specific wavelength for 10 minutes by using the LED light source. The LED source has the largest wattage: 1.0W, irradiation power intensity at 1.0 W: 35.4 mW/cm$^2$ (distance is 50 mm), the peak wavelength of red LED: 635 nm, the peak wavelength of blue LED: 405 nm, and, when it irradiates at a height about 50 mm from the bottom surface, it can irradiate with bottom of phi-6-cm dish, almost uniformly. In the example, it irradiated for 10 minutes with irradiation power 400 mW (irradiation power intensity 14.1 mW/cm$^2$) for red LED or blue LED. Then, the culture medium including ALA was removed, and 4 mL of culture medium for the stem cell or the somatic cell was added. It observed under the microscope after 24 hours to the time specified by each experiment. In this case, the number of survived cell is estimated by using Cell Counting Kit-8 (Dojindo Molecular Technologies, Inc., and hereinafter, it was called as "CCK8"). Also, evaluation of the undifferentiated state by expression of Alkaline phosphatase (hereinafter, it called as "ALP") was carried out by using Blue Alkaline Phosphatase Substrate Kit III (Cat. No. SK-5300, Vector (trademark) Inc.).

[Result]
(Evaluation of Effects of ALA for iPS Cell)

Firstly, ALA and/or SFC were added to the iPS cell, and it evaluated whether there was influenced or not when photoirradiation was not performed.

In detail, passage inoculation of the iPS cell was kept, the inoculation was performed and cultivated to a 60-mm dish, it exchanges for the culture medium added ALA and/or SFC, then it exchanges again for the culture medium added ALA and/or SFC if needed, and the cell form at the time of addition (0 hour), after 4 hours, after 24 hours, and after 48 hours were observed. PDT did not carry out in this experiment.

The culture condition is as follows: used cell line: 201B7, used culture-medium: Primate ES Cell Medium, addition concentration of ALA: 1000 micro-M, and addition concentration of SFC: 500 micro-M.

The result is explained with reference to FIG. 1 to FIG. 4.

FIG. 1 showed the photograph of the cell form at the time of ALA and/or SFC addition (0 hour). Each photograph in the figure showed the colony morphology of iPS cells by each combination of no added ALA (−) or added (+), no added SFC (−) or added (+). Also, in each combination, the upper photograph is a scale of 500 micrometers, and a lower photograph magnifies the corresponding upper photograph by a factor of two.

Figure 2:
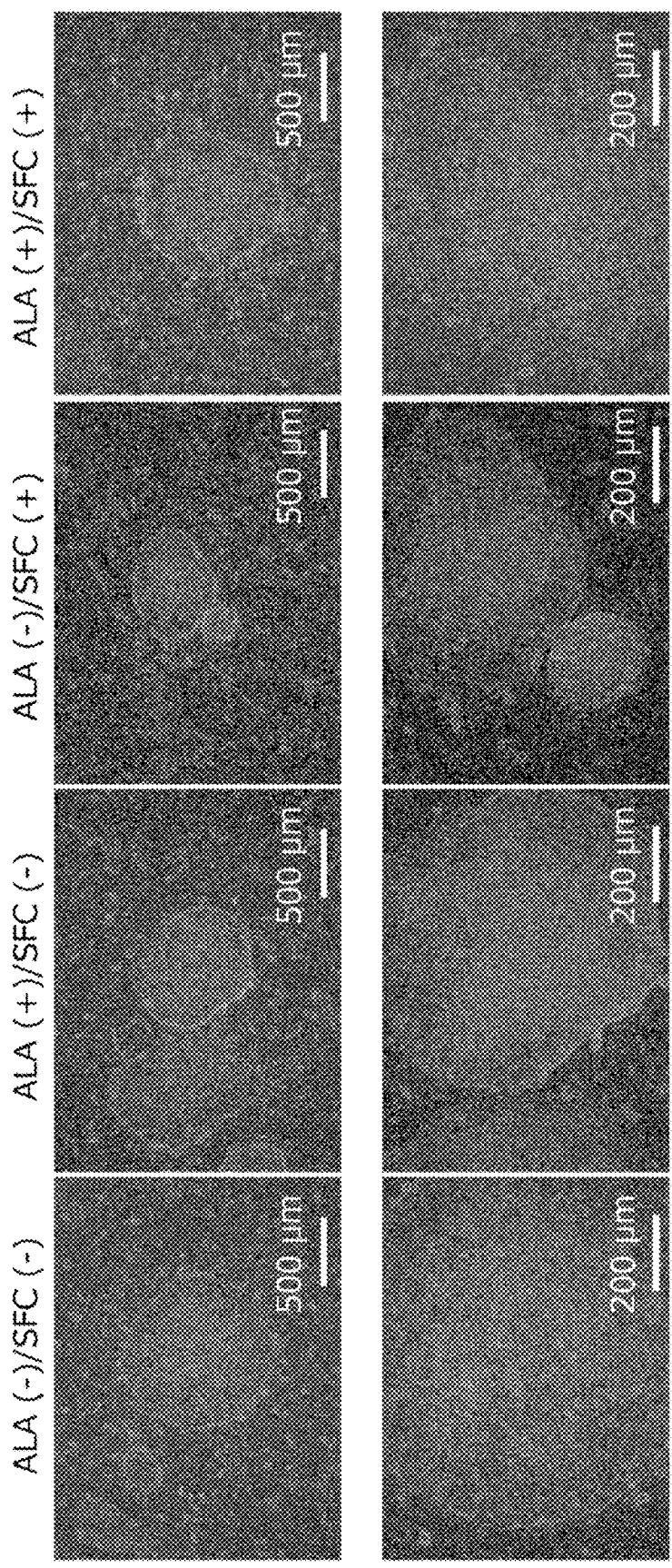
FIG. 2 is a photograph showing the iPS cell 4 hours after ALA addition in evaluation of the operation of ALA on the iPS cell according to Example 1 of the present invention.
Figure 3:
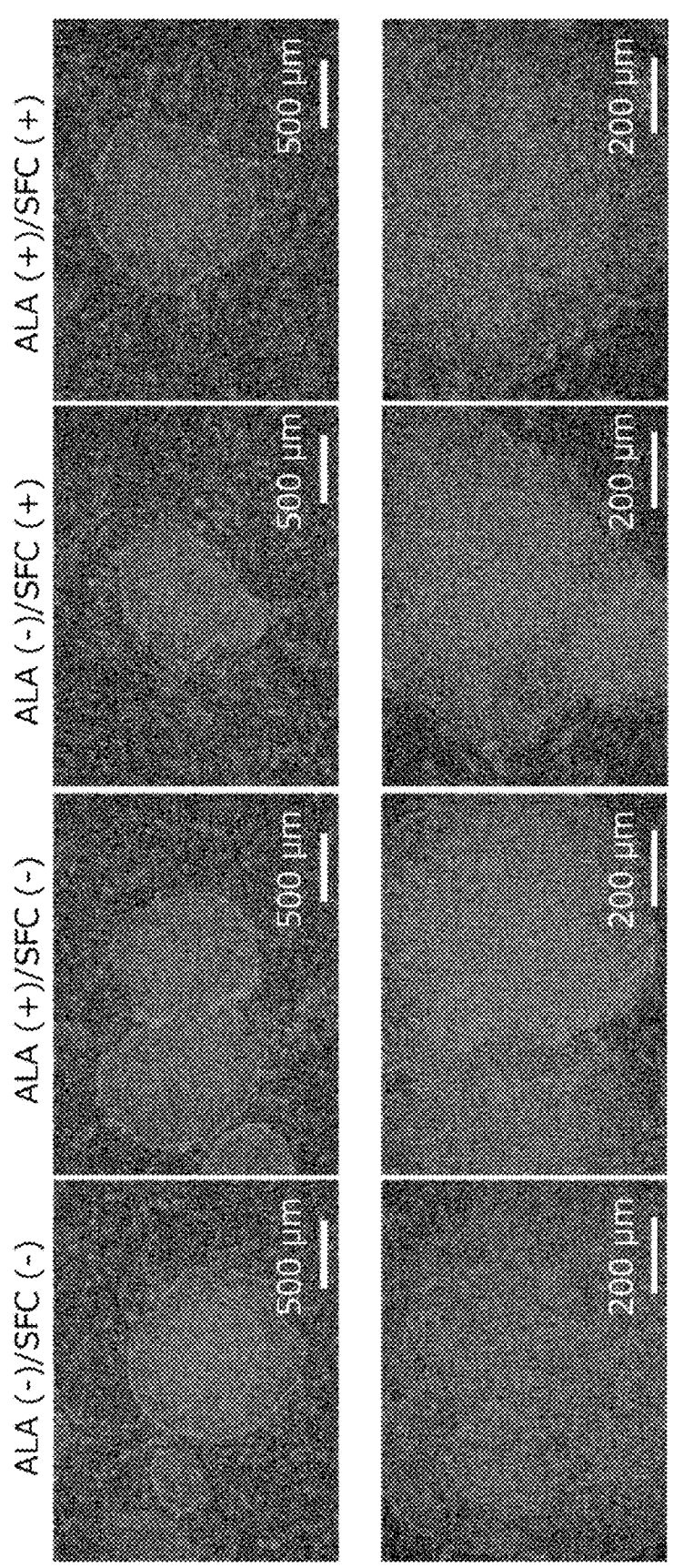
FIG. 3 is a photograph showing the iPS cell 24 hours after ALA addition in evaluation of the operation of ALA on the iPS cell according to Example 1 of the present invention.
Figure 4:
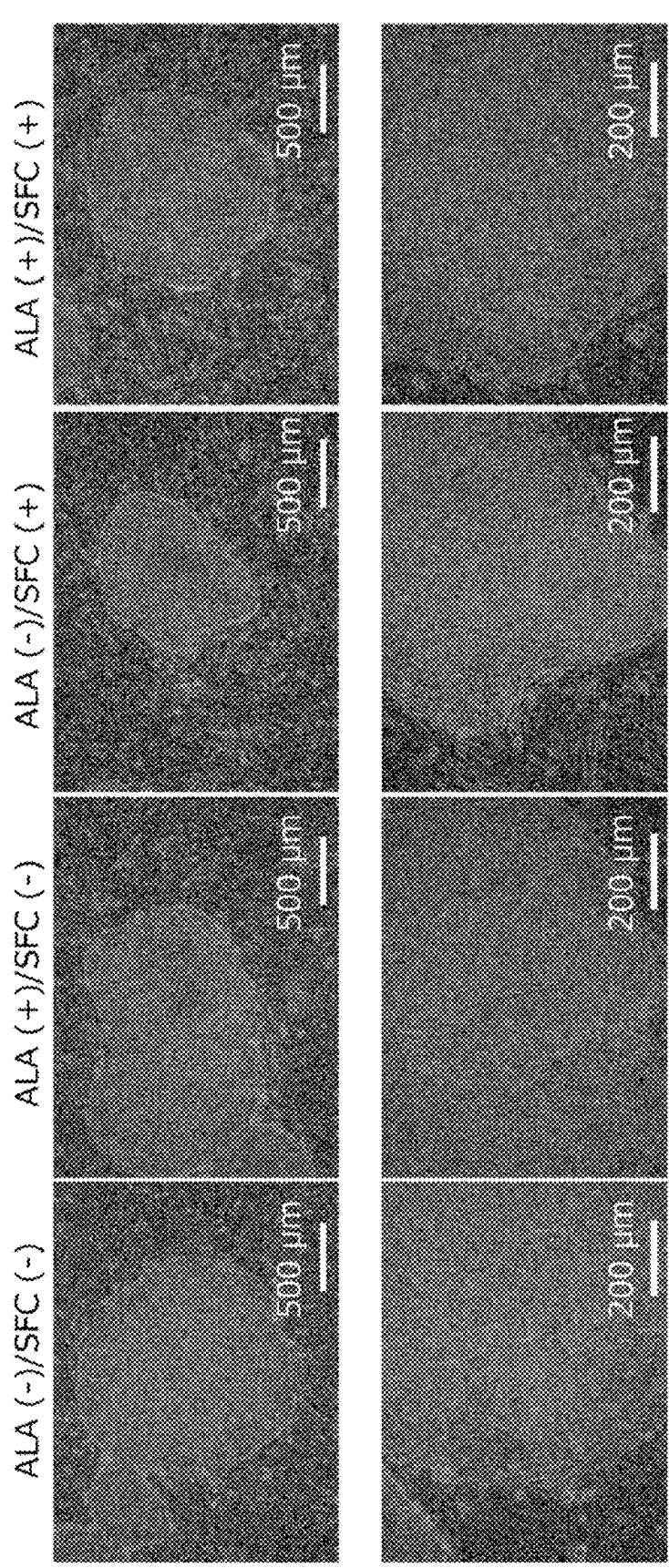
FIG. 4 is a photograph showing the iPS cell 48 hours after ALA addition in evaluation of the operation of ALA on the iPS cell according to Example 1 of the present invention.

FIG. 2 showed the colony morphology of the iPS cell 4 hours after adding ALA, similarly. FIG. 3 showed the colony morphology of the iPS cell 24 hours after. FIG. 4 showed the colony morphology of the iPS cell 48 hours after.

Also in either, the iPS cell showed the normal state being maintained undifferentiated form in view. That is, influence on the iPS cell was not observed. Therefore, ALA is considered to have no toxicity, or the like, to iPS when only ALA is added and no photoirradiation is performed.

(Evaluation of Effects of ALA-PDT for iPS Cell)

Then, by adding ALA and/or SFC to an iPS cell and by performing photoirradiation, an evaluation is performed whether any removal effect of the iPS cell is indicated or not.

In detail, passage inoculation of the iPS cell was performed, inoculation was performed to a 60-mm dish and was cultivated, it was exchanged for the culture medium added ALA and/or SFC, and then it kept cultivated for 48 hours. Then, it irradiated with blue LED (wavelength of 405 nm) for 10 minutes and observed the cell form 24 hours afterward.

Culture conditions were: used cell line: 201B7, used culture-medium: Primate ES Cell Medium, addition concentration of ALA: 1000 micro-M, and addition concentration of SFC: 500 micro-M.

The result is explained with reference to FIG. 5 to FIG. 8.

Figure 5:
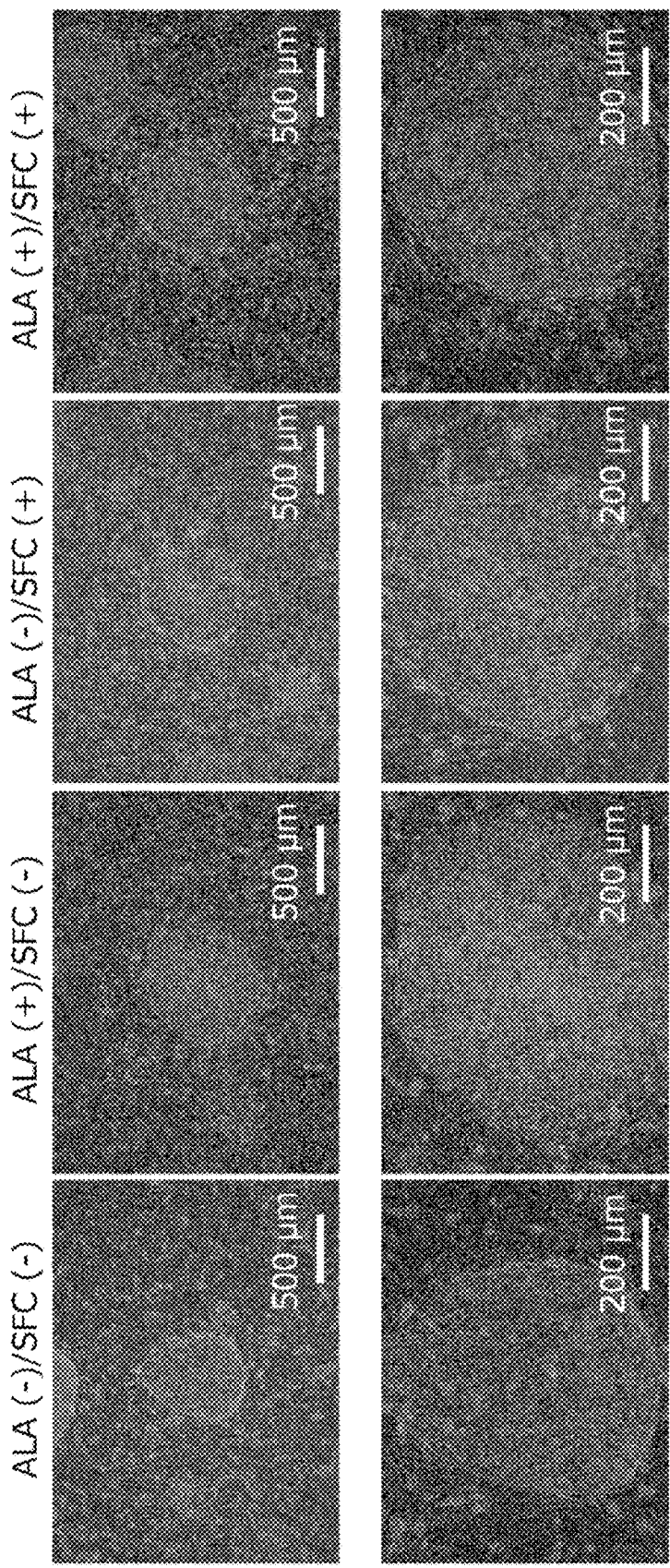
FIG. 5 is a photograph showing the iPS cell at the time of ALA and/or SFC addition (0 hour) in evaluation of an operation of ALA-PDT on the iPS cell according to Example 1 of the present invention.

FIG. 5 showed the photograph of the cell form at the time of ALA and/or SFC addition (0 hour). Each photograph is similar to the case of FIG. 1, and the iPS cell showed the normal state being maintained undifferentiated form in view.

Figure 6:
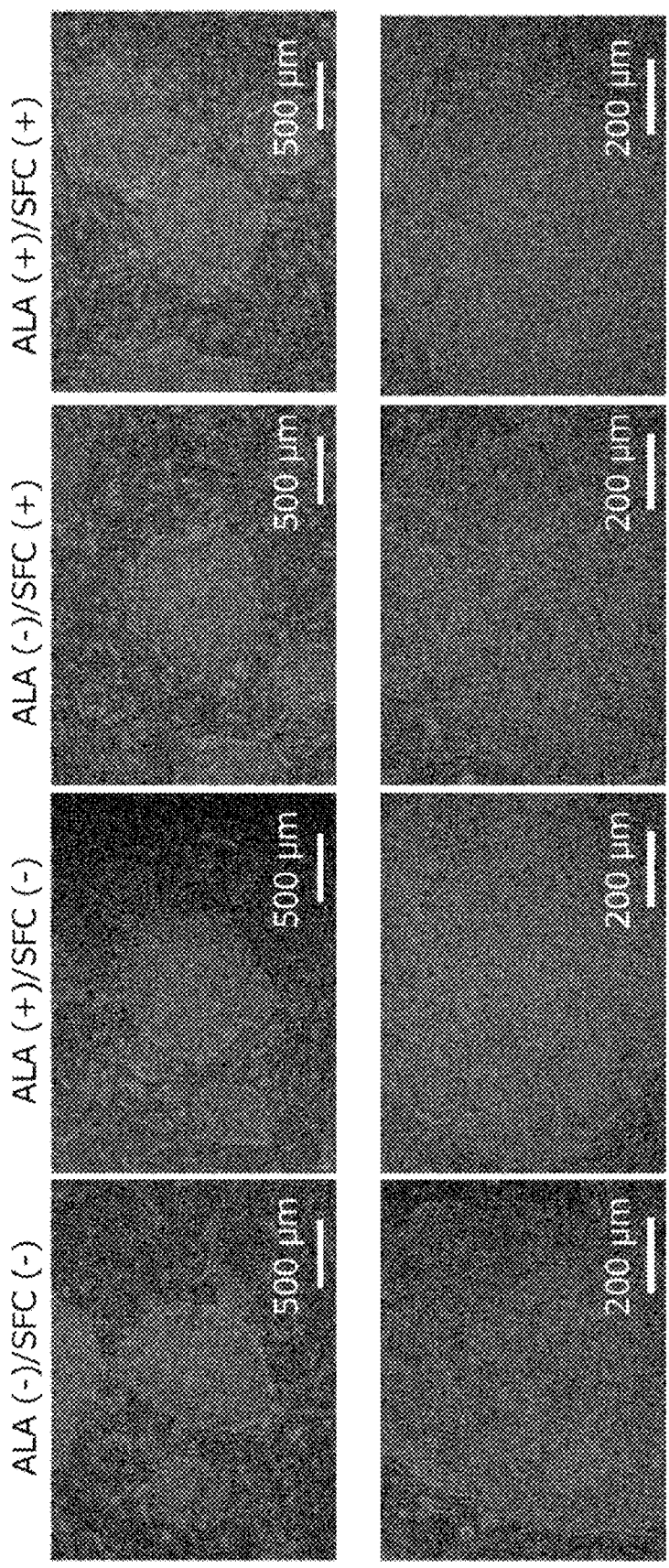
FIG. 6 is a photograph showing the iPS cell at the time of 48-hour progress after ALA and/or SFC addition in evaluation of the operation of ALA-PDT on the iPS cell according to Example 1 of the present invention.

FIG. 6 showed the photograph of the cell form of the iPS cell 48 hours after ALA and/or SFC addition. Even in this time, as similar to FIG. 4, the influence by ALA, and/or SFC addition 48 hours afterward was not observed, particularly.

FIG. 7 showed the photograph taken 24 hours after irradiating with blue LED for 10 minutes, which the irradiation was performed at the time of 48 hours after ALA and/or SFC addition. In the iPS cells added ALA (ALA (+)/SFC (−) ALA (+)/SFC (+)), it was observed that the colonies of the iPS cells collapsed, and a part of them was exfoliated.

FIG. 8 showed the result of evaluating the undifferentiated state by expression of ALP, about each colony in FIG. 7. In the iPS cell added ALA (ALA (+)/SFC (−)) and the iPS cell added ALA and SFC (ALA (+)/SFC (+)), each of them was lighter-colored than the case not-added (ALA (−)/SFC (−)) and showed that ALP became negative. This meant that it became impossible to maintain the undifferentiated state. Also, in the case only added SFC (ALA (−)/SFC (+)), it was deep-colored as like the case not added, and it was maintaining the undifferentiated-like state.

As a conclusion, after adding ALA and irradiating with the light of the specific wavelength, an undifferentiated iPS cell was no longer observed. That is, the undifferentiated iPS cell was removed.

(Comparison of Effects by Wavelength of Photoirradiation of ALA-PDT for iPS Cell)

Then, the effect by the difference of the wavelength in the photoirradiation of ALA-PDT for a human iPS cell was compared.

As the same as that of above-mentioned "evaluation of effect of ALA-PDT for iPS cell", passage inoculation of the iPS cell was performed, inoculation was performed to a 60-mm dish and was cultivated, it exchanged for the culture medium added ALA (100 micro-M or 1000 micro-M), and then it kept cultivated for 4 hours. Then, the cultured iPS cell was irradiated with red LED (wavelength of 635 nm) or blue LED (wavelength of 405 nm) for 10 minutes, and the cell form was observed 24 hours afterward.

Culture conditions were: used cell line: 201B7 and used culture-medium: Primate ES Cell Medium.

The result is explained with reference to FIG. 9 to FIG. 10.

FIG. 9 showed the photograph taken the result of the photoirradiation of blue LED or red LED for 10 minutes, 4 hours after adding ALA. Each photograph in the figure shows the form of the colony of the iPS cell by each combination of the addition volume of ALA (100 micro-M or 1000 micro-M), red LED (Red LED), and blue LED (Blue LED), respectively. Also, in each combination, the upper photograph is a scale of 500 micrometers, and a lower photograph magnifies the corresponding upper photograph by a factor of two. Also in blue LED, as almost the same as the red LED in FIG. 7, the effect that the colony collapsed by ALA-PDT was observed.

FIG. 10 shows the photograph for investigating expression of ALP by the kit about the result of FIG. 9. In each figure, the upper part shows a microphotograph and the lower part shows ALP expression on a dish. Among these, blue color was thinner, and thus it became impossible to maintain the undifferentiated state. The effect of ALA-PDT by the photoirradiation of blue LED was the almost same as the case of red LED.

(Comparison of Effects by ALA Concentration of ALA-PDT for iPS Cell)

Then, in ALA-PDT for the human iPS cell, the effects for changing the concentration of ALA were compared.

The iPS cell performed the passage process as well as an above-mentioned process was incubated for 2 to 4 minutes by using CTK (collagenase trypsin KSR) in 37 degree-C and then separated by pipetting. The separated iPS cell was inoculated 15,000 cells per well in 96 well plate, and then ALA hydrochloride was added into the cell and cultivated at the third day, and, 4 hours afterward, it irradiated with red LED for 10 minutes and added the solution of CCK8. The absorbance of 450 nm was measured with the plate leader 24 hours afterward, and the surviving cell number was counted.

This result is explained with reference to FIG. 11.

Figure 11:
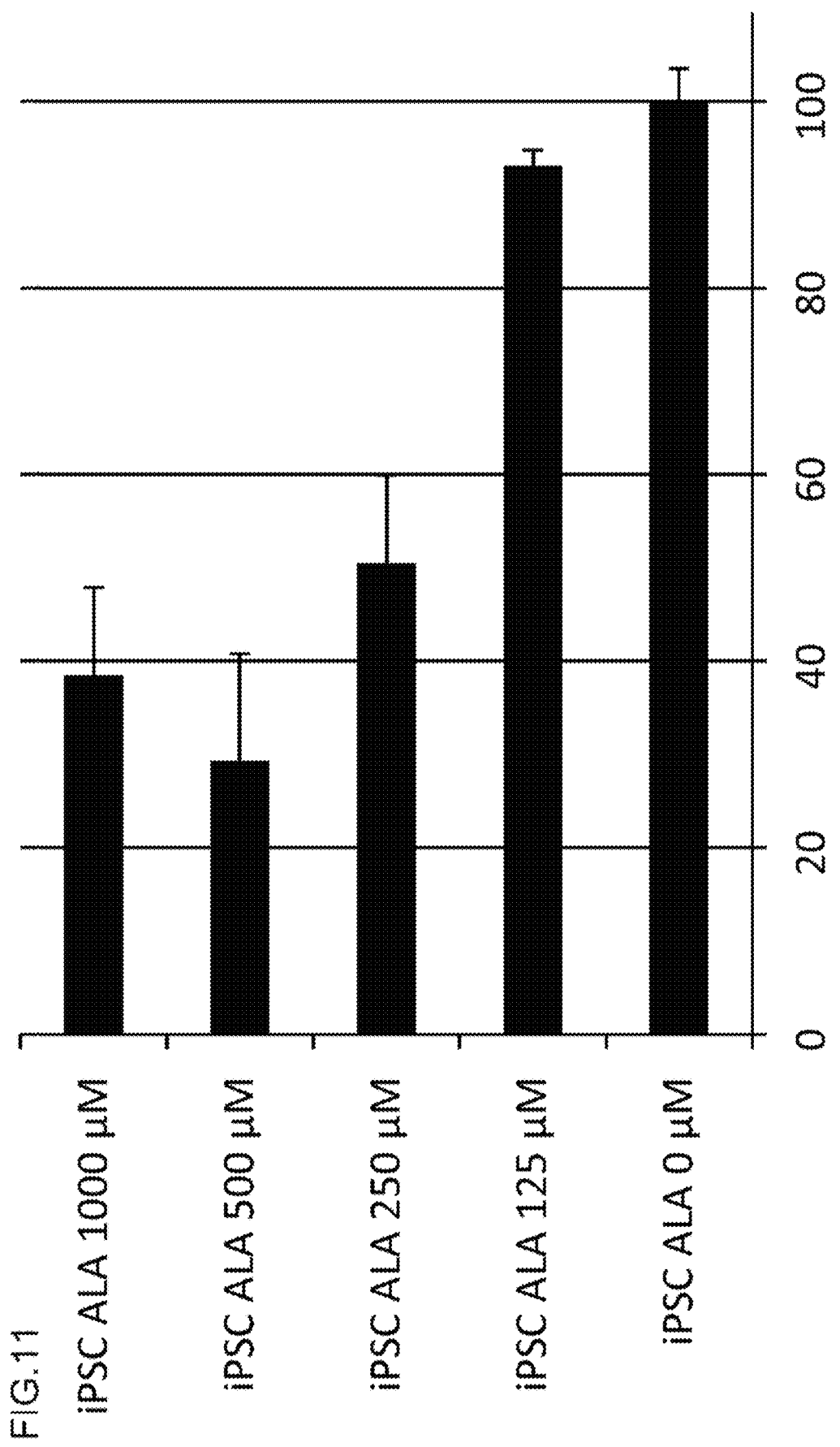
FIG. 11 is a graph showing a result of count number of survived iPS cell by CCK8 in comparison of the operation with the concentration of ALA in ALA-PDT on the iPS cell according to Example 1 of the present invention.

FIG. 11 showed the graph for the result of the count number by CCK8 for the iPS cell survived in the above-mentioned experiment. The vertical axis showed the concentration of ALA (0 micro-M, 125 micro-M, 250 micro-M, 500 micro-M, 1000 micro-M), and the horizontal axis showed the ratio of the cell number (rate of change) when the ALA concentration in each cell line is 0 micro-M as set to the value 1.0 (100%) (n=3).

According to the other experiment (not shown), induction of 10% or more cell death of iPS cell by ALA-PDT was observed at the concentration greater than or equal to about 100 micro-M. Also, at the concentration greater than or equal to 250 micro-M, the cell death of the iPS cell greater than or equal to the rate of 60% was induced. According to results of the inventors' experiments or the like (not shown), in the culturing condition that the 10% cell death of iPS cell occurs, the undifferentiated ability of the iPS cell is lost. Also, especially, in the culturing condition that the 60% cell death of iPS cell occurs, the undifferentiated ability of the iPS cell itself is lost, certainly. Therefore, it is possible to remove an iPS cell by ALA-PDT, certainly.

(Comparison of Effects by ALA Concentration of ALA-PDT for HDF)

Then, the effects of ALA-PDT were compared by using somatic cells other than the pluripotent stem cell or the somatic stem cell.

About a normal human dermal fibroblast (HDF), based on the equivalent conditions as above-mentioned "comparison of effects by ALA hydrochloride concentration and photoirradiation of ALA-PDT for iPS cell", the effects of the ALA concentration and ALA-PDT were compared.

This result is explained with reference to FIG. 12.

Figure 12:
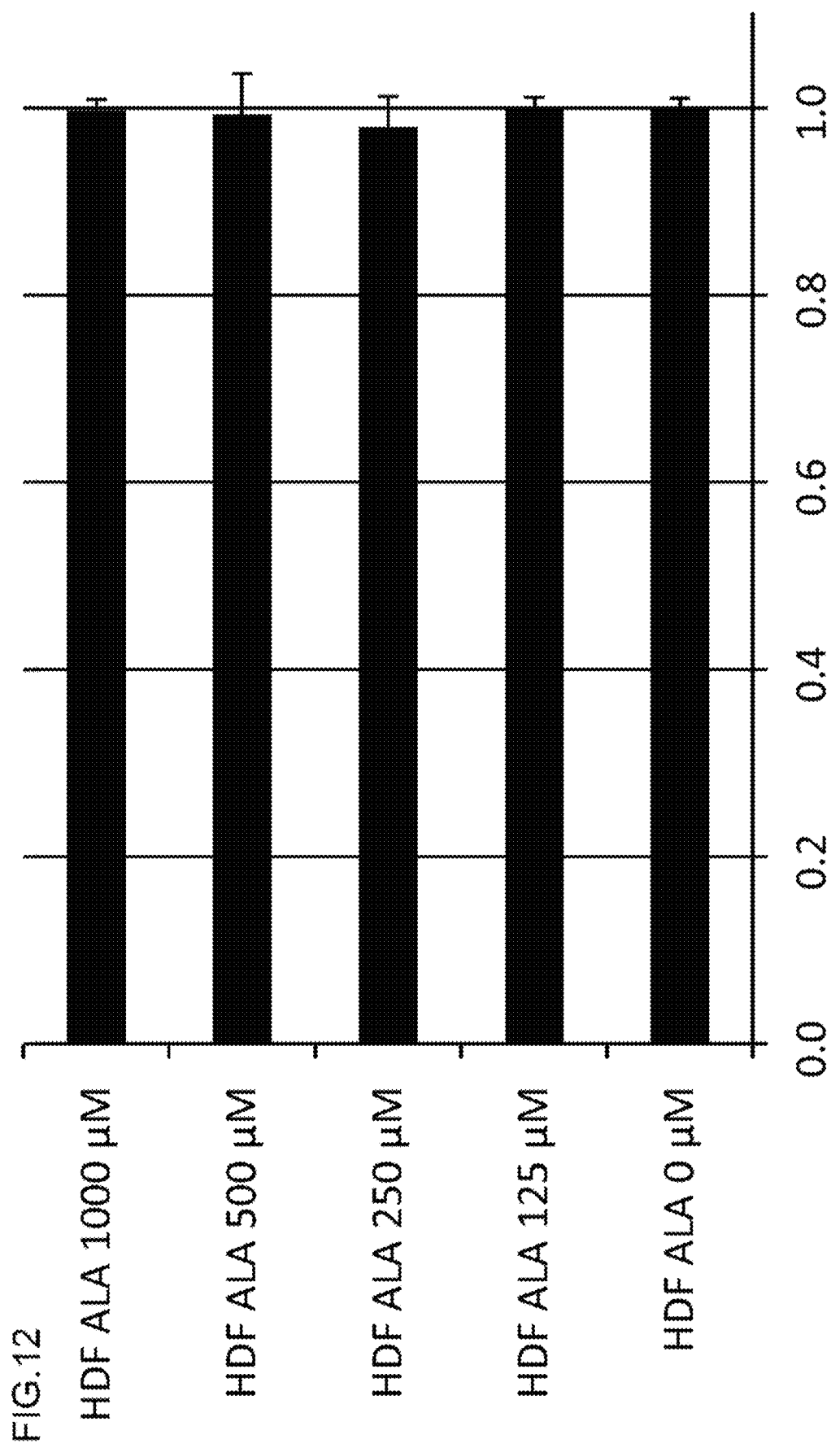
FIG. 12 is a graph showing a result of count number of survived HDF by CCK8 in comparison of the operation with the concentration of ALA in ALA-PDT on HDF according to Example 1 of the present invention.

FIG. 12 showed the graph for the result of the count number by CCK8 for the survived HDF in the above-mentioned experiment. The vertical axis showed the concentration of ALA, and the horizontal axis showed the ratio of the cell number (rate of change) when the ALA concentration in each cell line is 0 micro-M as set to the value 1.0 (100%) (n=3).

According to FIG. 12, in HDF, induction of the cell death by ALA-PDT was not observed. That is, when combined with the above results, it is possible to remove only the iPS cell by ALA-PDT without cell death of HDF.

(Evaluation of Effects of ALA-PDT for Neuron Originated from iPS Cell)

Then, the effects by ALA-PDT for the neuron performed differentiation induction from the human iPS cell (neuron originated from iPS cell) were evaluated. The used neuron was ReproNeuro. The neuron performed differentiation induction from the iPS cell was inoculated to a 60-mm dish and was cultured, it was exchanged for the culture medium added ALA (0 micro-M, 250 micro-M, 500 micro-M), and then it kept cultivated for 4 hours. After that, the cell form was observed. Then, the cultured neuron was irradiated with red LED (wavelength of 635 nm) for 10 minutes, and the cell form was observed after 12-hour progresses (overnight). Then, it was exchanged the culture medium, which ALA was not included, and the cell form was observed after cultivating with exchanging the culture media for seven days.

This result is explained with reference to FIG. 13 to FIG. 14.

Figure 13:
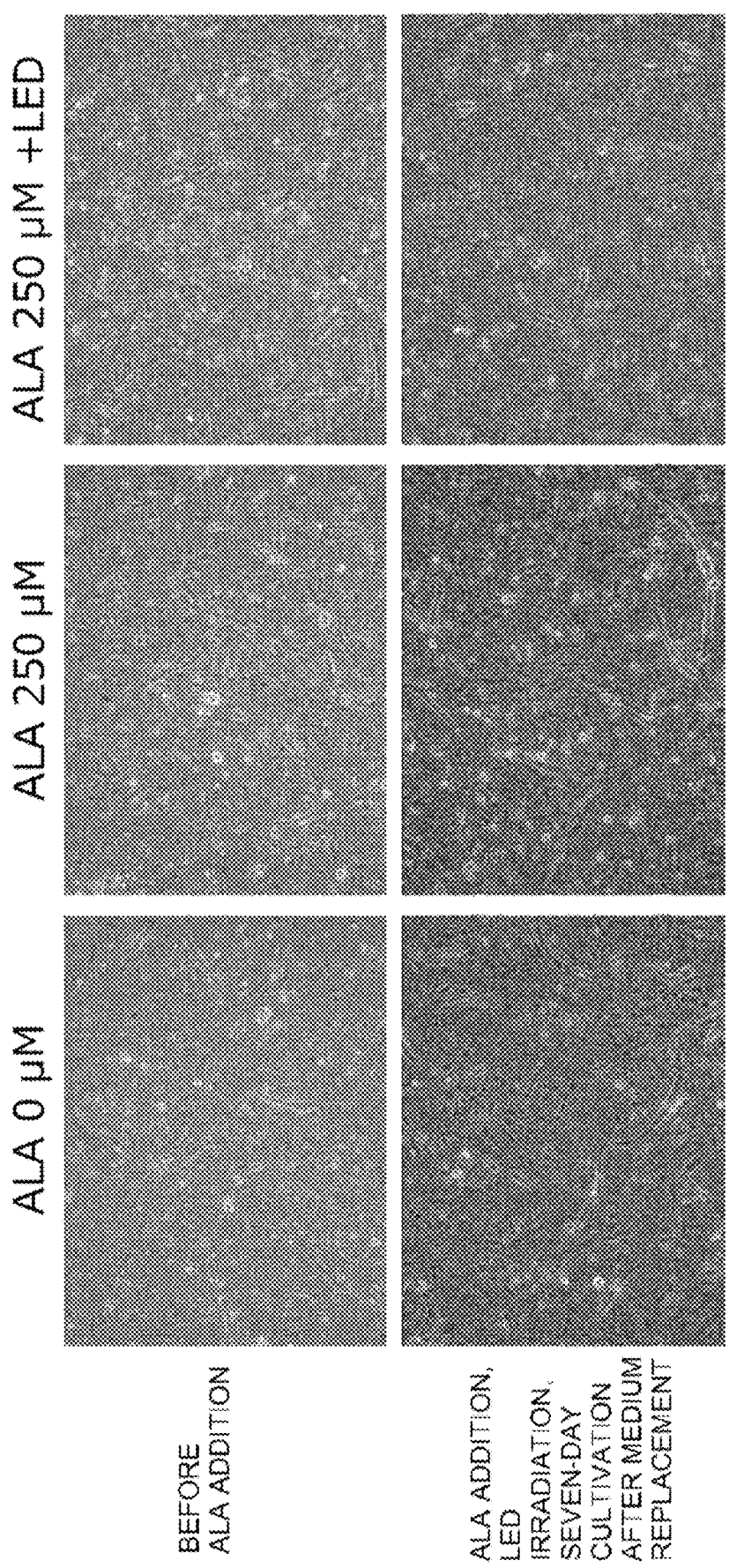
FIG. 13 is a photograph showing a neuron performed differentiation induction in the iPS cell in evaluation of an operation of ALA-PDT on the neuron originating in the iPS cell according to Example 1 of the present invention.

Each photograph of FIG. 13 showed the photograph for ALA concentration (0 micro-M, 250 micro-M, 500 micro-M), the upper part was before ALA addition, and the lower part was cultivated for seven days after ALA-PDT, respectively.

As for the neuron performed differentiation induction from the iPS cell, the neural spine became short, temporarily, by addition of ALA and LED irradiation (not shown). However, when the cultivation was continued for seven days, it continued surviving without extinction and recovered as like the condition before ALA addition.

FIG. 14 collected the above-mentioned result. The neuron performed differentiation induction from the iPS cell continued surviving although shortening of the neural spine was observed by ALA-PDT. That is, unlike the iPS cell, the neuron was not removed by ALA-PDT and was protected.

Also, seven days after adding 250 micro-M, 500 micro-M concentration of ALA, cell adhesion could be confirmed, and the neural spine was elongating in all of them. That is, by performing continuous cultivation, re-extension of a neural spine was observed and a human iPS cell origin neuron continued surviving, although shortening of the neural spine was seen by ALA-PDT.

(Evaluation of Effect of ALA-PDT for Cardiac Muscle Cell Originated from iPS Cell)

Then, the effects by ALA-PDT to the cardiac muscle cell performed differentiation induction from the human iPS cell (the cardiac muscle cell originated from the iPS cell) were evaluated. Here, a colony of the cardiac muscle cell performed differentiation induction from the iPS cell was obtained, inoculation was performed to a 60-mm dish and was cultivated, it exchanged for the culture medium added ALA (500 micro-M), and it cultivated for 4 hours and observed the cell form at that time. Then, it irradiated with red LED for 10 minutes and observed the cell form once again after 12-hour progresses (overnight).

This result is explained with reference to FIG. 15.

In FIG. 15, (a) was a photograph of a state of the colony for the cardiac muscle cell before ALA-PDT (before ALA exposure), and (b) was a photograph of the colony of the cardiac muscle cell after ALA-PDT (after 10-minute irradiation after ALA exposure). After ALA-PDT, the naturally-beating cardiac muscle stopped, and the cardiac muscle colony also lost its shape. Thereby, in ALA-PDT having 500 micro-M ALA concentration, it turned out that the cardiac muscle cell was not protected.

On the other hand, in the preliminary experiment (not shown), by ALA-PDT about 250 micro-M ALA concentration, the cardiac muscle cell recovered as like the neuron and beat by cultivating about several days after ALA-PDT. That is, by ALA-PDT having the concentration equal to or less than 250 micro-M, while protecting a cardiac muscle cell, the iPS cell could be removed from the above-mentioned result. On the contrary, the alternative removal by the type of cell can be performed by ALA-PDT greater than or equal to 500 micro-M, such that the cardiac muscle cell and the iPS cell were removed while protecting the HDF and the neuron.

Also, by a preliminary experiment, about the hepatic cells performed differentiation induction from the iPS cell (the hepatic cell originated from the iPS cell), as like the above-mentioned neuron, even if adding 250 micro-M concentration ALA, it was protected, and thus it could remove the iPS cell, selectively.

Example 2

(Other iPS Cell Line and Evaluation of Effects of ALA-PDT for after-Addition Time)

As pluripotent stem cell lines, separately, for 201B7 cell line, which is equivalent as above-mentioned Example 1, and for RC001 and RC010 (ReproCELL Inc.), after maintaining as like above-mentioned Example 1, evaluations of the ALA effects were performed. RC001 was originated from Fibroblast and was iPS cellularized by a retroviral vector as like the above-mentioned 201B7 cell line. Also, RC010 was originated from Endothelial progenitor cell (EPC) and was iPS cellularized by introduction of RNA.

About these lines, 20,000 cells were seeded per well in a 96-well plate and cultured for 3 to 4 days. Then, each of them was cultivated with culture medium added ALA hydrochloride having concentration (0, 125, 250, 500, 1000 micro-M), respectively. They were irradiated with red LED for 10 minutes after 4-hour cultivation or 24-hour cultivation by the above-mentioned culture medium. They were irradiated with red LED for 10 minutes by irradiation power 400 mW (irradiation power intensity 14.1 mW/cm$^2$). In each of them, the solution of CCK8 was added, the absorbance of 450 nm was measured with the plate leader after 24 hours, the surviving cell number was counted, and the cell survival rate after 24 hours was calculated.

The result is shown in the following table 1:

TABLE 1

| CELL LINE | ORIGINAL CELL | REPROGRAMING METHOD | INTRODUCING GENE | CULTURING METHOD | EFFECT BY ALA |
|---|---|---|---|---|---|
| 201B7 | Fibroblast | RETROVIRUS VECTOR | OCT3/4, Sox2, Klf4, c-Myc | ReproXF/ vitornectin | SURVIVAL/ PROLIFERATION SUPPRESSION |
| RC001 | Fibroblast | RETROVIRUS VECTOR | OCT3/4, Sox2, Klf4, c-Myc | ReproXF/ vitornectin | SURVIVAL/ PROLIFERATION SUPPRESSION |
| RC010 | Endothelial progenitor cell (EPC) | RNA | Oct4, Klf4, Sox2, c-Myc, Lin28 | ReproXF/ vitornectin | SURVIVAL/ PROLIFERATION SUPPRESSION |

Survival and proliferation for each cell line were suppressed by ALA-PDT as like in Example 1 as described above. That is, it was clear that ALA-PDT has common damaging effect on the iPS cell in a plurality of cell lines. Thereby, also in other iPS cells, the effects of ALA-PDT can be expected, generally.

Then, the effects by the difference in time until photoirradiation being performed after adding ALA to the iPS cell (after-addition time) were compared. That is, the suitable waiting time of performing photoirradiation after adding ALA to the iPS cell was examined.

Figure 16:
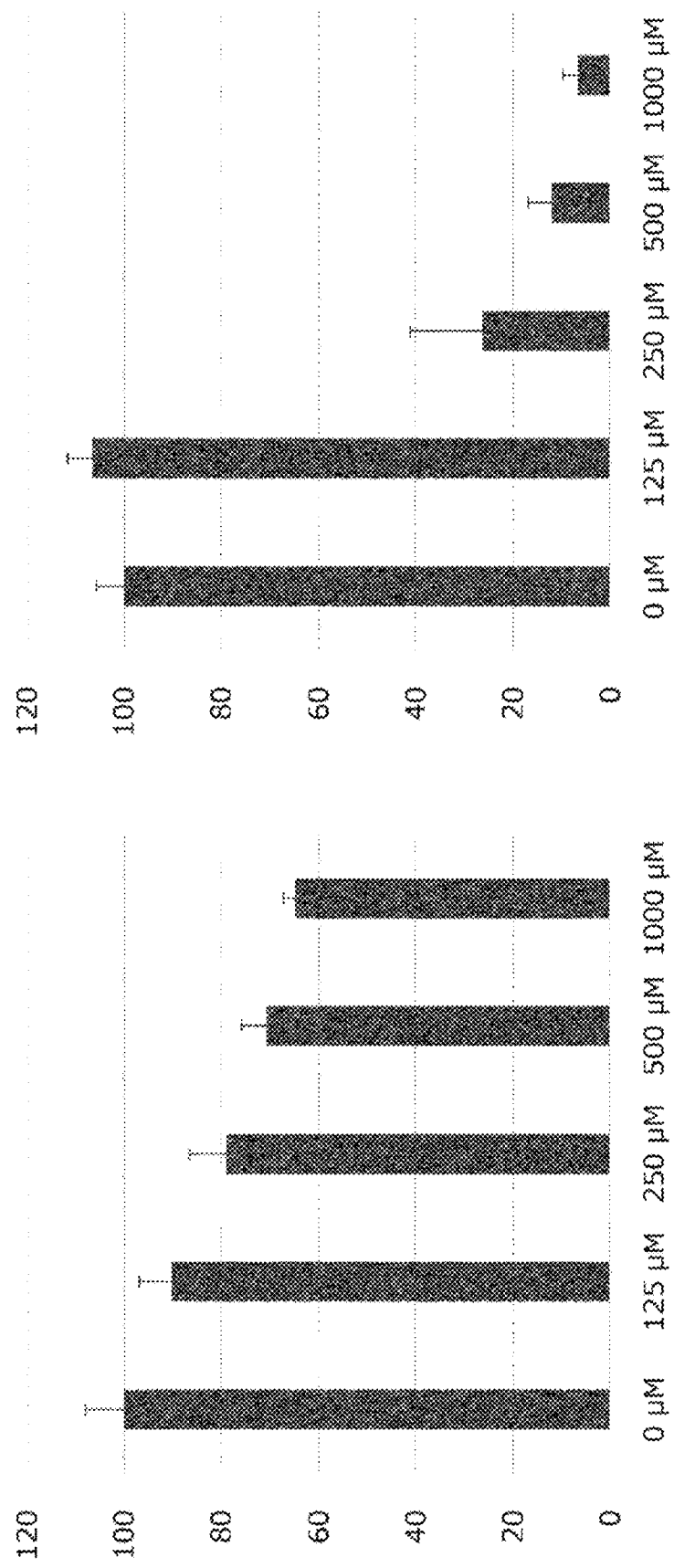
FIG. 16 is a graph showing probability of survival after ALA-PDT at the time of changing the time from addition of ALA on the iPS cell according to Example 2 of the present invention.

In FIG. 16, inoculating the above 201B7 cell line in a 96-well plate at 20,000 cells per well was performed, then ALA hydrochloride was added into the cell on the third day, then red LED was made to act for 10 minutes after 4 hours or 24 hours, and the result was evaluated by CCK8 on the fourth day. In each concentration, a bar of the graph showed a rate of change (%) when the value of 0 micro-M ALA addition (control) in each cell strain is set to 100. An error bar showed standard deviation (n=96).

As a result, in case of the after-addition time of ALA was 4 hours, the rate of cell survival of the iPS cell was decreased as compared with the control. As actually shown in FIG. 16 (a), when the 250 micro-M ALA was added and the photoirradiation was performed, and with the after-addition time for 4 hours, the rate of cell survival became 65% as compared with the control that did not perform photoirradiation.

Also, when photoirradiation was performed in 24 hours afterward, which the after-addition time of ALA was longer, it became possible to suppress cell survival and proliferation of the iPS cell at even lower concentration. As shown in FIG. 16 (b), after-addition time was 24 hours, the rate of cell survival became 7% as compared with the control.

In addition, by a preliminary experiment, even if it increases the after-addition time of ALA from 24 hours, there is no change the rate of cell survival as compared with that at 24 hours.

(Evaluation of Effect of ALA-PDT for Hepatic Cells of iPS Cell Origin)

The effect by ALA-PDT was evaluated for a hepatic cell originated from human iPS cell equivalent to the above-mentioned Example 1. At this example, the culture condition was plating 500,000 cells per well in a 24-well plate, then each concentration (0, 250, 500 micro-M) of ALA hydrochloride was added to the cell on the seventh day, photoirradiation was performed for 10 minutes by red LED 24 hours afterward, then form observation was carried out on the next day and after. The irradiation power of red LED was the same as that of above-mentioned case.

This result is shown in FIG. 17 and FIG. 18.

FIG. 17 was photographs of the plates of the hepatic cells originated from the human iPS cell when adding 250 micro-M ALA hydrochloride, (a) it was after 24-hour progress and is before photoirradiation (before LED irradiation), (b) it was after 24-hour progress of photoirradiation (24 hours after LED irradiation), and (c) it was after 48-hour progress after photoirradiation (48 hours after LED irradiation). In FIG. 17 (a), the cobblestone morphology and nucleus specifying to the hepatic cell could be clearly-confirmed. After the photoirradiation in FIG. 17 (b), even if 24 hours passed, the cell with clear cobblestone morphology and nucleus remained. Also, after photoirradiation in FIG. 17 (c), even if 48 hours passed, the cell with cobblestone morphology and nucleus continued surviving. Thereby, it confirmed that the differentiated hepatic cell originated from the human iPS cell was remained.

Also, FIG. 18 were photographs of the plate of the hepatic cells originated from the human iPS cell that, when changing the concentration of ALA hydrochloride to 0 micro-M, 250 micro-M, and 500 micro-M, before photoirradiation (before LED irradiation), after 24-hour progress of photoirradiation (after 24 hours LED irradiation), (c) after 60-hour progress of photoirradiation (after 60 hours LED irradiation). In these, the photograph of 250 micro-M showed the photograph of a plate other than in FIG. 17. It turned out that the hepatic cells originated from the human iPS cells survived under the various conditions of ALA-PDT were present. Also, in visual inspection, the state of the survived cells under the condition of 250 micro-M were better than that of 500 micro-M.

As a result, also about the hepatic cell originated from the iPS cell, as the same as that of the neuron in Example 1, a normal cell could be remained even if it added ALA having 250 micro-M concentration, and it was possible to have removed iPS cells other than the normal cell, selectively.

In addition, the configuration and operation of the above-mentioned embodiment are an example, it cannot be over-emphasized that it can change suitably and can execute in the range which does not deviate from the aim of the present invention.

INDUSTRIAL APPLICABILITY

The stem cell removing method in the present invention can culture a stem cell in vitro, after performing differentiation induction to a somatic cell, it can remove a stem cell easily, only the somatic cell performed differentiation induction can be introduced into a living body after that so as to use for the regenerative medicine, or the like, and it can use it on industry.

What is claimed is:

1. A method of removing pluripotent stem cells from culture, the method comprising:
    a) culturing mammalian pluripotent cells and somatic cells in culture medium containing aminolevulinic acid (ALA), a derivative of ALA, a salt of ALA, or a salt of a derivative of ALA; and
    b) irradiating the cells obtained in step a) such that the pluripotent cells are killed and the somatic cells are maintained in the culture.

2. The method of claim 1, wherein the pluripotent cells are embryonic stem (ES) cells or induced pluripotent stem (iPS) cells.

3. The method of claim 1, wherein the derivative of ALA has the structure of formula 1

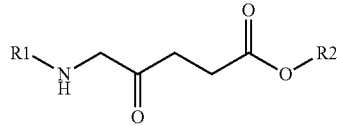

[Formula 1]

wherein R1 is a hydrogen atom, and R2 is a straight chain alkyl group.

4. The method of claim 1, wherein the concentration of the ALA, the derivative of ALA, the salt of ALA, or the salt of a derivative of ALA is 10-2000 µM.

5. The method of claim 1, wherein the cells are irradiated for 4 hours or more.

6. A composition comprising:
    a) mammalian pluripotent cells;
    b) mammalian somatic cells;
    c) culture medium; and
    d) aminolevulinic acid (ALA), a derivative of ALA, a salt of ALA, or a salt of a derivative of ALA.

7. The composition of claim 6, wherein the derivative of ALA has the structure of formula 1

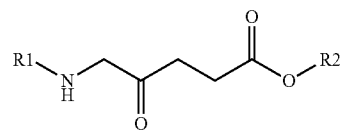

[Formula 1]

wherein R1 is a hydrogen atom, and R2 is a straight chain alkyl group.

8. The composition of claim 6, wherein the concentration of the ALA, the derivative of ALA, the salt of ALA, or the salt of a derivative of ALA is 10-2000 µM.

* * * * *